US007488735B2

(12) United States Patent
Prat Quinones

(10) Patent No.: US 7,488,735 B2
(45) Date of Patent: Feb. 10, 2009

(54) QUINUCLIDINE AMIDE DERIVATIVES

(75) Inventor: Maria Prat Quinones, Barcelona (ES)

(73) Assignee: Laboratorios Almirall S.A., Barcelona (ES)

( * ) Notice: Subject to any disclaimer, the term of this patent is extended or adjusted under 35 U.S.C. 154(b) by 387 days.

(21) Appl. No.: 10/518,714

(22) PCT Filed: Jun. 25, 2003

(86) PCT No.: PCT/EP03/06708

§ 371 (c)(1),
(2), (4) Date: Aug. 1, 2005

(87) PCT Pub. No.: WO2004/005285

PCT Pub. Date: Jan. 15, 2004

(65) Prior Publication Data

US 2006/0167042 A1    Jul. 27, 2006

(30) Foreign Application Priority Data

Jul. 2, 2002    (ES)    ............................ 200201539

(51) Int. Cl.
A01N 43/42    (2006.01)
A01N 43/90    (2006.01)
A61K 31/44    (2006.01)
C07D 453/02    (2006.01)
C07D 221/02    (2006.01)

(52) U.S. Cl. .................. 514/299; 514/305; 546/112; 546/137

(58) Field of Classification Search ............. 546/112, 546/137
See application file for complete search history.

(56) References Cited

U.S. PATENT DOCUMENTS 3,714,357 A    1/1973    Gueremy et al.

FOREIGN PATENT DOCUMENTS

| CA | 2155320 | 8/1993 |
|---|---|---|
| EP | 0 424 021 A1 | 4/1991 |
| EP | 0 747 355 A1 | 12/1996 |
| EP | 0 801 067 A1 | 10/1997 |
| EP | 0 863 141 A1 | 9/1998 |
| EP | 0 930 298 | 7/1999 |
| FR | 2012964 | 3/1970 |
| JP | 9-328469 | 12/1997 |
| WO | WO93/16048 | 8/1993 |
| WO | WO 01/04118 A2 | 1/2001 |
| WO | WO02/00652 | 1/2002 |
| WO | WO 02/051841 A1 | 7/2002 |
| WO | WO 02/053564 A2 | 7/2002 |

OTHER PUBLICATIONS

Sternbach et al., Journal of the American Chemical Society (1952), 74, 2219-21.*
International Search Report dated Sep. 10, 2003.
Abstract from Patent Abstracts of Japan for 09-328469, published Dec. 22, 1997.
L. Noronha-Blob et al., "Stereoselective antimuscarinic effects of 3-quinuclidinyl atrolactate and 3-quinuclidinyl xanthene-9-carboxylate", *European Journal of Pharmacology*, vol. 221, pp. 97-103, 1992.
S.H. Gao et al., "Stereochemistry of the Heterocyclic Alcohols Containing Piperidine Unit", *Chemical Journal of Chinese Universities*, vol. 20 No. 2, pp 232-236, 1999.
J. Lars et al., "Some quinuclidine derivatives with potential antimalarial activity", *Acta Pharm. Suecica*, vol. 5, pp. 71-76, 1968.
N.N. Godovikov, et al., "Synthesis and muscarinolytic activity of quinuclidinyl benzilate alkyl iodides", Khim. Farm. Zh., vol. 19, No. 9, pp. 1060-1061, 1985.
H. Konzett and R. Rössler, *Arch. Exp. Path. Pharmacol.*, 195, 71-74 (1940).
F. Leonard and I. Ehrenthal, *J. Am. Chem. Soc.*, vol. 73, 2216-2218 (1951).
E. Atkinson et al., *J. Med. Chem.*, vol. 20, No. 12, 1612-1617 (1977).
Waelbroeck et al., *Mol. Pharmacol.*, 38:267-273 (1990).
R. Eglen and S. Hedge, *Drug News Perspect.*, 10(8):462-469 (1997).
Chapter 6, "Cholinergic Transmission," in H. Rang et al., *Pharmacology*, Churchill Livingston, New York (1998).
Chapter 7, "Muscarinic Receptor Agonists and Antagonists," in Goodman and Gilman's *The Pharmacological Basis of Therapeutics*, 10th edition, McGraw Hill, New York (2001).

* cited by examiner

*Primary Examiner*—D. Margaret Seaman
*Assistant Examiner*—Niloofar Rahmani
(74) *Attorney, Agent, or Firm*—Finnegan, Henderson, Farabow, Garrett & Dunner, LLP

(57) ABSTRACT

New quinuclidine amide derivatives having the chemical structure of general formula (I) and pharmaceutically acceptable salts thereof including quaternary salts of formula (II) are disclosed; as well as processes for their preparation, pharmaceutical compositions 10 comprising them and their use in therapy as antagonists of M3 muscarinic receptors.

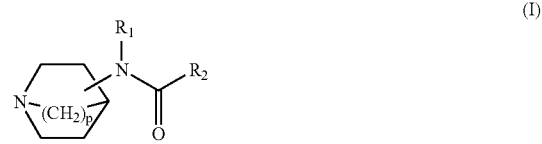

(I)

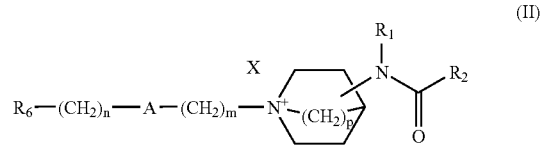

(II)

10 Claims, No Drawings

QUINUCLIDINE AMIDE DERIVATIVES

This application is a national stage filing under 35 U.S.C. § 371 of International Application No. PCT/EP2003/006708, filed on Jun. 25, 2003. This application claims the benefit of priority under 35 U.S.C. § 119 to Spanish Patent Application No. P200201539 filed on Jul. 2, 2002.

This invention relates to new therapeutically useful quinuclidine amide derivatives, to some processes for their preparation and to pharmaceutical compositions containing them.

The novel structures according to the invention are antimuscarinic agents with a potent and long lasting effect. In particular, these compounds show high affinity for M3 muscarinic receptors. This subtype of muscarinic receptor is present in glands and smooth muscle and mediates the excitatory effects of the parasympathetic system on glandular secretion and on the contraction of visceral smooth muscle (Chapter 6, Cholinergic Transmission, in H. P. Rang et al., Pharmacology, Churchill Livingstone, N.Y., 1995).

M3 antagonists are therefore known to be useful for treating diseases characterised by an increased parasympathetic tone, by excessive glandular secretion or by smooth muscle contraction (R. M. Eglen and S. S. Hegde, (1997), Drug News Perspect., 10(8):462-469).

Examples of this kind of diseases are respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia (Chapter 7, Muscarinic Receptor Agonists and Antagonists, in Goodman and Gilman's The Pharmacological Basis of Therapeutics, 10th edition, McGraw Hill, New York, 2001).

The compounds of the invention can be used alone or in association with other drugs commonly regarded as effective in the treatment of these diseases. For example, they can be administered in combination with $\beta_2$-agonists, steroids, antiallergic drugs, phosphodiesterase IV inhibitors and/or leukotriene D4 (LTD4) antagonists for simultaneous, separate or sequential use in the treatment of a respiratory disease.

The new quinuclidine amide derivatives of the invention have the chemical structure of formula (I):

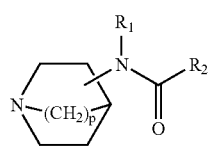

(I)

wherein
$R_1$ represents a hydrogen atom or a straight or branched, optionally substituted lower alkyl group;
$R_2$ represents a group of formula i) or ii)

i)

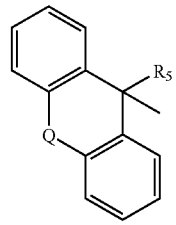

ii)

wherein
$R_3$ represents a group selected from phenyl, 2-furyl, 3-furyl, 2-thienyl or 3-thienyl;
$R_4$ represents a group selected from optionally substituted lower alkyl, optionally substituted lower alkenyl, optionally substituted lower alkynyl, cycloalkyl, cycloalkylmethyl, phenyl, benzyl, phenethyl, 2-fury, 3-furyl, 2-thienyl or 3-thienyl;
and $R_5$ represents a hydrogen atom or a hydroxy, methyl, or —$CH_2OH$ group;
the benzene rings in formula ii) and the cyclic groups represented by $R_3$ and $R_4$ being each independently optionally substituted by one, two or three substituents selected from halogen, straight or branched, optionally substituted lower alkyl, hydroxy, straight or branched, optionally substituted lower alkoxy, nitro, cyano, —$CO_2R'$ or —$NR'R''$, wherein $R'$ and $R''$ each independently represents a hydrogen atom or a straight or branched, optionally substituted lower alkyl group or $R'$ and $R''$ together with the atom to which they are attached form a cyclic group;
Q represents a single bond or a —$CH_2$—, —$CH_2$—$CH_2$—, —O—, —O—$CH_2$—, —S—, —S—$CH_2$— or —CH=CH— group;
p is 1 or 2 and the amide group is at positions 2, 3 or 4 of the azabicyclic ring;
or pharmaceutically acceptable salts thereof; including quaternary ammonium salts;
and all individual stereoisomers and mixtures thereof;
with the proviso that when p is 2, the amide moiety is in position 3 of the quinuclidine ring, $R_1$ is hydrogen and $R_3$ and $R_4$ are both unsubstituted phenyl, then
when said compound is not a pharmaceutically acceptable salt or is a HCl salt, then $R_5$ cannot be one of hydrogen or hydroxy; and
when said compound is a quaternary ammonium salt having a methyl group attached to the nitrogen atom of the quinuclidine ring, then $R_5$ cannot be hydroxy.

The compounds of the invention include quaternary ammonium salts of formula (II).

(II)

$R_6$—$(CH_2)_n$—A—$(CH_2)_m$—N⁺—...

wherein $R_1$, $R_2$ and p are as defined above;
m is an integer from 0 to 8;
n is an integer from 0 to 4:

A represents a group selected from —CH$_2$—, —CH=CR'—, —CR'=CH—, —CR'R"—, —C(O)—, —O—, —S—, —S(O)—, —S(O)$_2$— and —NR'—, wherein R' and R" are as defined above;

R$_6$ represents a hydrogen atom, or a group selected from straight or branched, optionally substituted lower alkyl, hydroxy, straight or branched, optionally substituted lower alkoxy, cyano, nitro, —CH=CR'R", —C(O)OR', —OC(O)R', —SC(O)R', —C(O)NR'R", —NR'C(O)OR", —NR'C(O)NR", cycloalkyl, phenyl, naphthanelyl, 5,6,7,8-tetrahydronaphthanelyl, benzo[1,3]dioxolyl, heteroaryl or heterocyclyl; R' and R" being as defined above; and wherein the cyclic groups represented by R$_6$ are optionally substituted by one, two or three substituents selected from halogen, hydroxy, straight or branched, optionally substituted lower alkyl, phenyl, —OR', —SR', —NR'R", —NHCOR', —CONR'R", —CN, —NO$_2$ and —COOR'; R' and R" being as defined above;

X$^-$ represents a pharmaceutically acceptable anion of a mono or polyvalent acid.

and all individual stereoisomers and mixtures thereof;

with the proviso that when p is 2, the amide moiety is in position 3 of the quinuclidine ring, R$_1$ is hydrogen, R$_3$ and R$_4$ are both unsubstituted phenyl and R$_5$ is hydroxy, then in the compounds of formula (II) the sequence R$_6$—(CH$_2$)$_n$-A-(CH$_2$)$_m$— cannot be a methyl group.

Further objectives of the present invention are to provide processes for preparing said compounds; pharmaceutical compositions comprising an effective amount of said compounds; the use of the compounds in the manufacture of a medicament for the treatment of diseases susceptible of being improved by antagonism of M3 muscarinic receptors; and methods of treatment of diseases susceptible to amelioration by antagonism of M3 muscarinic receptors, which methods comprise the administration of the compounds of the invention to a subject in need of treatment.

Certain quinuclidine amide derivatives, which fall outside the scope of the present invention, have been disclosed in JP 09328469 and WO 9316048.

As used herein, an alkyl group or moiety can be straight or branched, and is typically a lower alkyl group or moiety. A lower alkyl group or moiety contains 1 to 8, preferably 1 to 6 and more preferably 1 to 4 carbon atoms. In particular it is preferred that such an alkyl group or moiety is represented by a methyl, ethyl, propyl, including i-propyl or butyl, including n-butyl, sec-butyl and tert-butyl group or moiety.

As used herein, an alkenyl group or moiety can be straight or branched, and is typically a lower alkenyl group or moiety. A lower alkenyl group or moiety contains 2 to 8, preferably 2 to 6 and more preferably 2 to 4 carbon atoms. In particular it is preferred that such an alkenyl group or moiety is represented by a vinyl, allyl or 1-propenyl group or moiety.

As used herein, an alkynyl group or moiety can be straight or branched, and is typically a lower alkynyl group or moiety. A lower alkynyl group or moiety contains 2 to 8, preferably 2 to 6 and more preferably 2 to 4 carbon atoms. In particular it is preferred that such an alkynyl group or moiety is represented by a 3-butynyl or 1-propynyl group or moiety.

Optionally substituted lower alkyl, alkenyl or alkynyl groups mentioned herein include straight or branched lower alkyl, alkenyl or alkynyl groups as defined above, which may be unsubstituted or substituted in any position by one or more substituents, for example by 1, 2 or 3 substituents. When two or more substituents are present, each substituent may be the same or different. The substituent(s) are typically halogen atoms, preferably fluoride atoms, and hydroxy or alkoxy groups.

Alkoxy groups mentioned herein are typically lower alkoxy groups, that is groups containing from 1 to 8, preferably 1 to 6 and more preferably 1 to 4 carbon atoms, the hydrocarbon chain being branched or straight and optionally substituted in any position by one or more substituents, for example by 1, 2 or 3 substituents. When two or more substituents are present, each substituent may be the same or different. The substituent(s) are typically halogen atoms, most preferably fluoride atoms, and hydroxy groups. Preferred optionally substituted alkoxy groups include methoxy, ethoxy, n-propoxy, i-propoxy, n-butoxy, sec-butoxy, t-butoxy, trifluoromethoxy and difluoromethoxy, hydroxymethoxy, hydroxyethoxy or 2-hydroxypropoxy.

Cyclic groups mentioned herein include carbocyclic and heterocyclic groups. The cyclic groups can contain one or more rings. Carbocyclic groups may be aromatic or alicyclic, for example cycloalkyl groups. Heterocyclic groups also include heteroaryl groups.

Cycloalkyl groups and alicyclic groups mentioned herein, unless otherwise specified, typically contain from 3 to 7 carbon atoms. Cycloalkyl groups and alicyclic rings of 3 to 7 carbon atoms include cyclopropyl, cyclobutyl, cyclopentyl, cyclohexyl and cycloheptyl.

As used herein an aromatic group typically contains from 5 to 14, preferably 5 to 10 carbon atoms. Examples of aromatic groups include phenyl and naphthalenyl.

A heterocyclic or heteroaromatic group mentioned herein is typically a 5 to 10 membered group, such as a 5, 6 or 7 membered group, containing one or more heteroatoms selected from N, S and O. Typically, 1, 2, 3 or 4 heteroatoms are present, preferably 1 or 2 heteroatoms. A heterocyclic or heteroaromatic group may be a single ring or two or more fused rings wherein at least one ring contains a heteroatom. Examples of heterocyclic groups include piperidyl, pyrrolidyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, tetrazolyl, thienyl and dioxolyl. Examples of heteroaromatic groups include pyridyl, thienyl, furyl, pyrrolyl, imidazolyl, benzothiazolyl, pyridinyl, pyrazolyl, pyrazinyl, pyrimidinyl, pyridazinyl, indolyl, indazolyl, purinyl, quinolyl, isoquinolyl, phthalazinyl, naphthyridinyl, quinoxalinyl, quinazolinyl, cinnolinyl, triazolyl and pyrazolyl.

As used herein a halogen atom includes a fluorine, chlorine, bromine or iodine atom, typically a fluorine, chlorine or bromine atom.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic and nitric acid and organic acids, for example citric, fumaric, formic, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, aralkyl amines and heterocyclic amines. Preferred salts of the compounds of formula (I) are those formed between the nitrogen atom of the azabicyclic ring and an inorganic or an organic acid Other preferred salts according to the invention are quaternary ammonium compounds of formula (II), wherein an equivalent of an anion (X$^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, formate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

Preferred compounds of formulae (I) or (II) are those wherein $R_1$ is hydrogen, methyl or ethyl, most preferably hydrogen.

In some preferred embodiments of the invention $R_2$ is a group of formula i), wherein $R_3$ is a group, which is optionally substituted with one or more halogen atom(s), selected from phenyl, 2-thienyl, 3-thienyl or 2-furyl. More preferably $R_2$ is a group of formula i), wherein $R_3$ represents a group phenyl, 2-thienyl or 2-furyl which are optionally substituted with one or more halogen atom(s). Most preferably, $R_3$ is phenyl or 2-thienyl, Further preferred compounds having a group of formula i) are those wherein $R_4$ represents a linear group selected from ethyl, n-butyl, vinyl, allyl, 1-propenyl and 1-propynyl, or a group, which is optionally substituted with one or more halogen atom(s), methyl or methoxy group(s), selected from cyclopentyl, cyclohexyl, phenyl, benzyl, phenethyl, 2-thienyl and 3-furyl. More preferably compounds having a group of formula i) are those wherein $R_4$ represents a linear group selected from ethyl, n-butyl, vinyl, allyl and 1-propynyl, or a group, which is optionally substituted with one or more halogen atom(s), methyl or methoxy group(s), selected from cyclopentyl, phenyl, benzyl, phenethyl and 2-thienyl Most preferably, $R_4$ is ethyl, n-butyl, vinyl, allyl, cyclopentyl, phenyl, benzyl or 2-thienyl.

In other preferred embodiments of the invention $R_2$ is a group of formula ii), wherein Q represents a single bond or an oxygen atom.

In the most preferred embodiments of the invention $R_5$ in groups i) or ii) is a hydrogen atom or a hydroxy group.

Preferably, in the compounds of formulae (I) or (II) p is 2 and the amide group is at positions 3 or 4 of the azabicyclic ring, most preferably at position 3.

Particularly preferred compounds of formula (II) are those wherein m is an integer from 0 to 6 and n is an integer from 0 to 4; most preferably m is 0 to 5 and n 0 to 2; A represents a group selected from —$CH_2$—, —CH=CH—, —O—, —C(O)—, —NR'—, and —S—; most preferably A is —$CH_2$—, —CH=CH—, —O—; and $R_6$ is a hydrogen atom, a cyano group, a nitro group, a —C(O)OR' group, a —OC(O)R' group, a —SC(O)R', group, a —CH=$CH_2$ group, a —CH=CR'R" group, a C(O)NR'R" group, a straight or branched $C_1$-$C_4$ alkyl group, which is optionally substituted with one or more halogen atom(s), a straight $C_1$-$C_4$ alkoxy group, which is optionally substituted with one or more halogen atom(s) or hydroxy group(s), or a cyclic group, which is optionally substituted with one or more substituents selected from halogen atoms, groups of formula —C(O)NR'R" or methyl, hydroxy, nitro or phenyl groups, the cyclic group being selected from cyclohexyl, phenyl, 5,6,7,8-tetrahydronaphthanelyl, 2-thienyl, 1-pyrrolidinyl, 1-pyrrolyl, benzo [1,3]dioxolyl, 2-benzothiazolyl, naphthalenyl and dioxolyl. More preferably compounds of formula (II) are those wherein m is an integer from 0 to 5 and n is an integer from 0 to 2; A represents a group selected from —$CH_2$—, —CH=CH—, —O—, —C(O)—, —NR'—, and —S—; and $R_6$ is a hydrogen atom, a cyano group, a —C(O)OR' group, a —OC(O)R' group, a —SC(O)R', group, a —CH=$CH_2$ group, a —C(O) NR'R" group, a straight or branched $C_1$-$C_4$ alkyl group, a trifluoromethyl, or a cyclic group selected from cyclohexyl, 5,6,7,8-tetrahydronaphthanelyl, 2-thienyl, 1-pyrrolyl, benzo [1,3]dioxolyl, 2-benzothiazolyl, naphthalenyl, dioxolyl and phenyl, which is optionally substituted with one or more substituents selected from halogen atoms, groups of formula —C(O)NR'R", methyl, hydroxy and phenyl groups. Most preferably $R_6$ is selected from hydrogen, straight $C_1$-$C_4$ alkyl, —CH=$CH_2$, cyclohexyl, phenyl which is unsubstituted or substituted with one or two substituents selected from methyl groups and hydroxy groups, 5,6,7,8-tetrahydronaphthanelyl and 2-thienyl.

Most preferred are compounds of formula (II) wherein the sequence $R_6$—$(CH_2)_n$-A-$(CH_2)_m$— is one of methyl, 3-phenoxypropyl, 3-(3-hydroxyphenoxy)propyl, allyl, heptyl, 3-phenylpropyl, 3-phenylallyl, 2-phenoxyethyl, 2-benzyloxyethyl, cyclohexylmethyl, 3-(5,6,7,8tetrahydronaphthalen-2-yloxy)propyl, 5-(2,6dimethylphenoxy)pentyl, 3-thien-2-ylpropyl or 3-cyclohexylpropyl and $X^-$ is bromide or trifluoroacetate.

The compounds of the present invention represented by formulae (I) or (II) described above may have one or more asymmetric atoms, e.g. the carbon in position 3 of the quinuc0lidine ring; the carbon substituted by $R_3$, $R_4$ and $R_5$ in the compounds wherein $R_2$ is a group of formula i); or the carbon which is attached to the carbonyl group in the compounds wherein $R_2$ is a group of formula ii). Each of these asymmetric atoms may have R- or S-configuration. The single isomers and mixtures of the isomers fall within the scope of the invention.

Particular individual compounds of formula (I) include:
N-(1-Azabicyclo[2.2.2]oct-3-yl)-2-hydroxy-2,2-dithien-2-ylacetamide
N-[(3R)-1-Azabicyclo[2.2.2]oct-3-yl]-2-hydroxy-2,2-dithien-2-ylacetamide
N-[(3S)-1-Azabicyclo[2.2.2]oct-3-yl]-2-hydroxy-2,2-dithien-2-ylacetamide
N-[(3R)-1-Azabicyclo[2.2.2]oct-3-yl]-2,2-dithien-2-ylacetamide
N-[(3R)-1-Azabicyclo[2.2.2]oct-3-yl]-2-dyclopentyl-2-hydroxy-2-thien-2-ylacetamide
N-[(3R)-1-Azabicyclo[2.2.2]oct-3yl]-2-hydroxy-2-thien-2-ylpent4-enamide
(2*)-N-[(3R)-1-Azabicyclo[2.2.2]oct-3-yl]-2-hydroxy-2-thien-2-ylbutanamide (diastereomer 1)
(2*)-N-[(3R)-1-Azabicyclo[2.2.2]oct-3-yl]-2-hydroxy-2-thien-2-ylbutanamide (diastereomer 2)
(2*)-N-[(3R)-1-Azabicyclo[2.2.2]oct-3-yl]-2-hydroxy-2-thien-2-ylbut-3-enamide (diastereomer 1)
(2*)-N-[(3R)-1-Azabicyclo[2.2.2]oct-3-yl]-2-hydroxy-2-thien-2-ylbut-3-enamide (diastereomer 2)
N-[(3R)-1-Azabicyclo[2.2.2]oct-3-yl]-2,3-diphenylpropanamide
N-[(3R)-1-Azabicyclo[2.2.2]oct-3-yl]-2-cyclopentyl-2-hydroxy-2-phenylacetamide
N-[(3R)-1-Azabicyclo[2.2.2]oct-3-yl]-2-phenylhexanamide
N-(1-Azabicyclo[2.2.2]oct-3-yl)-9H-xanthene-9carboxamide
N-[(3R)-1-Azabicyclo[2.2.2]oct-3-yl]-9H-xanthene-9-carboxamide
N-[(3S)-1-Azabicyclo[2.2.2]oct-3-yl]-9H-xanthene-9-carboxamide
N-(1-Azabicyclo[2.2.2]oct-3-yl)-9-hydroxy-9H-fluorene-9-carboxamide
N-1-Azabicyclo[2.2.2]oct-3-yl-N-methyl-9H-xanthene-9-carboxamide N-1-Azabicyclo[2.2.2]oct-3-yl-N-ethyl-9H-xanthene-9car-
boxamide
N-1-Azabicyclo[2.2.2]oct-4-yl-2-cyclopentyl-2-hydroxy-2-
thien-2-ylacetamide
N-[(3R)-1-Azabicyclo[2.2.2]oct-3-yl]-2-hydroxy-2-phenyl-
2-thien-2-ylacetamide
N-[(3R)-1-Azabicyclo[2.2.2]oct-3-yl]-2-(5-bromothien-2-
y)-2-(4-fluoro-3-methylphenyl)-2-hydroxyacetamide
N-[(3R)-1-Azabicyclo[2.2.2]oct-3-yl]-2-fur-2-yl-2-hy-
droxypent-3-ynamide
N-[(3R)-1-Azabicyclo[2.2.2]oct-3-yl]-2-fur-2-yl-2-hy-
droxy-4-(4-methoxyphenyl)butanamide
N-[(3R)-1-Azabicyclo[2.2.2]oct-3-yl]-2-fur-3-yl-2-hy-
droxy-2-thien-2-ylacetamide
N-[(3R)-1-Azabicyclo[2.2.2]oct-3-yl]-2-cyclohexyl-2-hy-
droxy-2-thien-3-ylacetamide
N-[(3R)-1-Azabicyclo[2.2.2]oct-3-yl]-9-hydroxy-9H-fluo-
rene-9-carboxamide
N-[(3R)-1-Azabicyclo[2.2.2]oct-3-yl]-N-methyl-9H-xan-
thene-9-carboxamide
(2S)-N-[(3R)-1-azabicyclo[2.2.2]oct-3-y]-2-cyclopentyl-2-
hydroxy-2-thien-2-ylacetamide
((*) Configuration not assigned; either the (2R)- or the
(2S)-isomers of the above compounds may be produced).
Particular individual compounds of formula (II) include:
3-(2-Hydroxy-2,2-dithien-2-ylacetylamino)-1-methyl-1-
azoniabicyclo[2.2.2]octane bromide
3-(2-Hydroxy-2,2-dithien-2-ylacetylamino)-1-(3-phenox-
ypropyl)-1-azoniabicyclo[2.2.2]octane bromide
(3R)-3-(2-Hydroxy-2,2-dithien-2-ylacetylamino)-1-methyl-
1-azoniabicyclo[2.2.2]octane trifluoroacetate
(3R)-1-Allyl-3-(2-hydroxy-2,2-dithien-2-ylacetylamino)-1-
azoniabicyclo[2.2.2]octane trifluoroacetate
(3R)-1-Heptyl-3-(2-hydroxy-2,2-dithien-2-ylacetylamino)-
1-azoniabicyclo[2.2.2]octane trifluoroacetate
(3R)-3-(2-Hydroxy-2,2-dithien-2-ylacetylamino)-1-(3-phe-
nylpropyl)-1-azoniabicyclo[2.2.2]octane bromide
(3R)-3-(2-Hydroxy-2,2-dithien-2-ylacetylamino)-1-((E)-3-
phenylallyl)-1-azoniabicyclo[2.2.2]octane trifluoroacetate
(3R)-3-(2-Hydroxy-2,2-dithien-2-ylacetylamino)-1-(2-phe-
noxyethyl)-1-azoniabicyclo[2.2.2]octane bromide
(3R)-3-(2-Hydroxy-2,2-dithien-2-ylacetylamino)-1-(3-phe-
noxypropyl)-1-azoniabicyclo[2.2.2]octane bromide
(3R)-3-(2-Hydroxy-2,2-dithien-2-ylacetylamino)-1-[3-(3-
hydroxyphenoxy)propyl]-1-azoniabicyclo[2.2.2]octane
trifluoroacetate
(3R)-1-(2-Benzyloxyethyl)-3-(2-hydroxy-2,2-dithien-2-
ylacetylamino)-1-azoniabicyclo[2.2.2]octane trifluoroac-
etate
(3R)-3-(2-Hydroxy-2,2-dithien-2-ylacetylamino)-1-(3thien-
2-ylpropyl)-1-azoniabicyclo[2.2.2]octane bromide
(3S)-3-(2-Hydroxy-2,2-dithien-2-ylacetylamino)-1-(3-phe-
noxypropyl)-1-azoniabicyclo[2.2.2]octane bromide
(3R)-3-(2,2-Dithien-2-ylacetylamino)-1-(3-phenoxypro-
pyl)-1-azoniabicyclo[2.2.2]octane bromide
1-Methyl-3-[(9H-xanthen-9-ylcarbonyl)amino]-1-azoniabi-
cyclo[2.2.2]octane bromide
1-(3-Phenoxypropyl)-3-[(9H-xanthen-9-ylcarbonyl)amino]-
1-azoniabicyclo[2.2.2]octane bromide
(3R)-1-(3-Phenoxypropyl)-3-[(9H-xanthen-9-ylcarbonyl)
amino]-1-azoniabicyclo[2.2.2]octane bromide
(3S)-1-Allyl-3-[(9H-xanthen-9-ylcarbonyl)amino]-1-azoni-
abicyclo[2.2.2]octane trifluoroacetate
(3S)-1-Heptyl-3-[(9H-xanthen-9-ylcarbonyl)amino]-1-azo-
niabicyclo[2.2.2]octane trifluoroacetate
(3S)-1-Cyclohexylmethyl-3-[(9H-xanthen-9-ylcarbonyl)
amino]-1-azoniabicyclo[2.2.2]octane trifluoroacetate
(3S)-1-(3-Cyclohexylpropyl)-3-[(9H-xanthen-9-ylcarbonyl)
amino]-1-azoniabicyclo[2.2.2]octane trifluoroacetate
(3S)-1-(3-Phenoxypropyl)-3-[(9H-xanthen-9-ylcarbonyl)
amino]-1-azoniabicyclo[2.2.2]octane bromide
(3S)-1-[3-(5,6,7,8-Tetrahydronaphthalen-2-yloxy)propyl]-
3-[(9H-xanthen-9-ylcarbonyl)amino]-1-azoniabicyclo
[2.2.2]octane trifluoroacetate
(3S)-1-[5-(2,6-Dimethylphenoxy)pentyl]-3-[(9H-xanthen-
9-ylcarbonyl)amino]-1-azoniabicyclo[2.2.2]octane trif-
luoroacetate
3-{[(9-Hydroxy-9H-fluoren-9-yl)carbonyl]amino}-1-me-
thyl-1-azoniabicyclo[2.2.2]octane bromide
3{[(9-Hydroxy-9H-fluoren-9-yl)carbonyl]amino}-1-(3-phe-
noxypropyl)-1-azoniabicyclo[2.2.2]octane bromide
(3R)-1-[3-(2-Carbamoylphenoxy)propyl]-3-{[(9-Hydroxy-
9H-fluoren-9-yl)carbonyl]amino}-1-azoniabicyclo[2.2.2]
octane trifluoroacetate
(3R)-1-[4(4-Fluorophenyl)-4-oxobutyl]-3-{[(9-Hydroxy-
9H-fluoren-9-yl)carbonyl]amino}-1-azoniabicyclo[2.2.2]
octane trifluoroacetate
(3R)-3-{[(9-Hydroxy-9H-fluoren-9-yl)carbonyl]amino}-1-
(4-oxo-4-thien-2-ylbutyl)-1-azoniabicyclo[2.2.2]octane
trifluoroacetate
(3R)-3-{[(9-Hydroxy-9H-fluoren-9-yl)carbonyl]amino}-1-
3-(methylphenylamino)propyl]-1-azoniabicyclo[2.2.2]
octane trifluoroacetate
(3R)-3-{[(9-Hydroxy-9H-fluoren-9-yl)carbonyl]amino}-1-
(3-phenylsulfanylpropyl)-1-azoniabicyclo[2.2.2]octane
trifluoroacetate
3-[Methyl-(9H-xanthen-9-ylcarbonyl)amino]-1-(3-pyrrol-1-
ylpropyl)-1-azoniabicyclo[2.2.2]octane trifluoroacetate
1-[3-(Biphenyl-4-yloxy)propyl]-3-[ethyl-(9H-xanthen-9-yl-
carbonyl)amino]-1-azoniabicyclo[2.2.2]octane trifluoro-
acetate
(3R)-1-[3-(Benzo[1,3]dioxol-5-yloxy)propyl]-3-(2-hy-
droxy-2-phenyl-2-thien-2-ylacetylamino)-1-azoniabicy-
clo[2.2.2]octane trifluoroacetate
(3R)-1-[3-(Benzothiazol-2-yloxy)propyl]-3-(2-hydroxy-2-
phenyl-2-thien-2-ylacetylamino)-1-azoniabicyclo[2.2.2]
octane trifluoroacetate
(3R)-3-(2-Fur-2-yl-2-hydroxypent-3-ynoylamino)-1-[3-
(naphthalen-1-yloxy)propyl]-1-azoniabicyclo[2.2.2]oc-
tane trifluoroacetate
(3R)-3-[2-Fur-2-yl-2-hydroxy-4-(4-methoxyphenyl)butyry-
lamino]-1-[6-(4-phenylbutoxy)hexyl]-1-azoniabicyclo
[2.2.2]octane trifluoroacetate
(3R)-3-(2-Cyclopentyl-2-hydroxy-2-thien-2-ylacety-
lamino)-1-(2-hydroxyethyl)-1-azoniabicyclo[2.2.2]oc-
tane trifluoroacetate
(3R)-3-(2-Cyclopentyl-2-hydroxy-2-thien-2-ylacety-
lamino)-1-(2-ethoxyethyl)-1-azoniabicyclo[2.2.2]octane
trifluoroacetate
(3R)-3-(2-Cyclopentyl-2-hydroxy-2-thien-2-ylacety-
lamino)-1-{2-[2-(2-hydroxyethoxy)ethoxy]ethyl}-11-azo-
niabicyclo[2.2.2]octane trifluoroacetate
(3R)-3-(2-Cyclopentyl-2-hydroxy-2-thien-2-ylacety-
lamino)-1-(4,4,4-trifluorobutyl)-1-azoniabicyclo[2.2.2]
octane trifluoroacetate
(3R)-1-(4-Acetoxybutyl)-3-[2-(5-bromothien-2-yl)-2-(4-
fluoro-3-methylphenyl)-2-hydroxyacetylamino]-1-azoni-
abicyclo[2.2.2]octane trifluoroacetate
(3R)-3-[2-(5-Bromothien-2-yl)-2-(4fluoro-3-methylphe-
nyl)-2-hydroxyacetylamino]-1-(4-ethoxycarbonylbutyl)-
1-azoniabicyclo[2.2.2]octane trifluoroacetate
(3R)-1-(3-Acetylsulfanylpropyl)-3-[2-(5-bromothien-2-yl)-
2-(4-fluoro-3-methylphenyl)-2-hydroxyacetylamino]-1-
azoniabicyclo[2.2.2]octane trifluoroacetate (3R)-1-(3-Cyanopropyl)-3-(2-hydroxy-2-phenyl-2-thien-2-ylacetylamino)-1-azoniabicyclo[2.2.2]octane trifluoroacetate (3R)-1-(2-Carbamoylethyl)-3-(2-hydroxy-2-thien-2-ylpent-4-enoylamino)-1-azoniabicyclo[2.2.2]octane trifluoroacetate (3R)-1-(2-[1,3]Dioxolan-2-ylethyl)-3-(2-hydroxy-2-thien-2-ylpent-4-enoylamino)-1-azoniabicyclo[2.2.2]octane trifluoroacetate 4-(2-Cyclopentyl-2-hydroxy-2-thien-2-ylacetylamino)-1-(4-methylpent-3-enyl)-1-azoniabicyclo[2.2.2]octane trifluoroacetate (3R)-1-[3-(2-Carbamoylphenoxy)propyl]-3{[(9-Hydroxy-9H-fluoren-9-yl)carbonyl]amino}-1-azoniabicyclo[2.2.2]octane formate (3R)-1-[4-(4-Fluorophenyl)4-oxobutyl]-3-{[(9-Hydroxy-9H-fluoren-9-yl)carbonyl]amino}-1-azoniabicyclo[2.2.2]octane formate (3R)-3{[(9-Hydroxy-9H-fluoren-9-yl)carbonyl]amino}-1-[3-(methylphenylamino)propyl]-1-azoniabicyclo[2.2.2]octane chloride (3R)-3-{[(9-Hydroxy-9H-fluoren-9-yl)carbonyl]amino}-1-(3-phenylsulfanylpropyl)-1-azoniabicyclo[2.2.2]octane formate (3R)-3-[Methyl-(9H-xanthen-9-ylcarbonyl)amino]-1-(3-pyrrol-1-ylpropyl)-1-azoniabicyclo[2.2.2]octane bromide (3R)-1-[3-(Biphenyl-4-yloxy)propyl]-3-[methyl-(9H-xanthene-9-carbonyl)amino]-1-azoniabicyclo[2.2.2]octane chloride (3R)-3-(2-Fur-2-yl-2-hydroxypent-3-ynoylamino)-1-[3-(naphthalen-1-yloxy)propyl]-1-azoniabicyclo[2.2.2]octane chloride (3R)-1-[3-(Benzo[1,3]dioxol-5-yloxy)propyl]-3-(2-fur-2-yl-2-hydroxypent-3-ynoylamino)-1-azonia-bicyclo[2.2.2]octane bromide (3R)-1-[3-(Benzothiazol-2-yloxy)propyl]-3-(2-fur-2-yl-2-hydroxypent-3-ynoylamino)-1-azonia-bicyclo[2.2.2]octane chloride (3R)-3{[(2S)-2-Cyclopentyl-2-hydroxy-2-thien-2-ylacetyl]amino}-1-(2-hydroxyethyl)-1-azoniabicyclo[2.2.2]octane bromide (3R)-3-{[(2S)-2-Cyclopentyl-2-hydroxy-2-thien-2-ylacetyl]amino}-1-(2-ethoxyethyl)-1-azoniabicyclo[2.2.2]octane formate (3R)-3-{[(2S)-2-Cyclopentyl-2-hydroxy-2-thien-2-ylacetyl]amino}-1-(4,4,4-trifluorobutyl)-1-azoniabicyclo[2.2.2]octane bromide (3R)-1-(4-Acetoxybutyl)-3-[2-(5-bromothien-2-yl)-2-(4-fluoro-3-methylphenyl)-2-hydroxyacetylamino]-1-azoniabicyclo[2.2.2]octane bromide (3R)-3-[2-(5-Bromothien-2-yl)-2-(4fluoro-3-methylphenyl)-2-hydroxyacetylamino]-1-(4-ethoxycarbonylbutyl)-1-azoniabicyclo[2.2.2]octane bromide (3R)-1-(3-Acetylsulfanylpropyl)-3-[2-(5-bromothien-2-yl)-2-(4-fluoro-3-methylphenyl)-2-hydroxyacetylamino]-1-azoniabicyclo[2.2.2]octane formate (3R)-1-(3-Cyanopropyl)-3-[2-fur-2-yl-2-hydroxy4-(4-methoxyphenyl)butyrylamino]-1-azoniabicyclo[2.2.2]octane bromide (3R)-1-(2-Carbamoylethyl)-3-[2-fur-2-yl-2-hydroxy4-(4-methoxyphenyl)butyrylamino]-1-azoniabicyclo[2.2.2]octane formate (3R)-1-(2-[1,3]Dioxolan-2-yl-ethyl)-3-[2-fur-2-yl-2-hydroxy-4-(4-methoxyphenyl)butyrylamino]-1-azoniabicyclo[2.2.2]octane bromide In accordance with another embodiment, the present invention provides processes for preparing the novel quinuclidine amide derivatives of formulae (I) and (II)

The compounds of formula (I) may be prepared from the corresponding carboxylic acid of formula (III) following two different methods (a) and (b), illustrated in the following scheme.

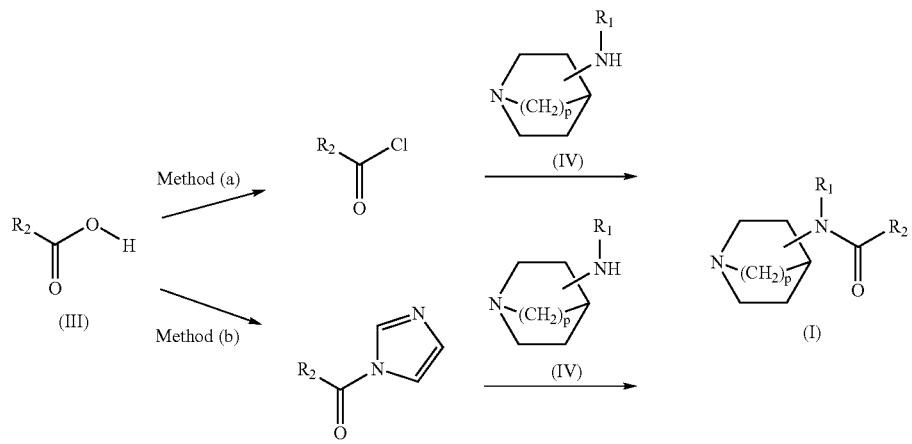

Some compounds of formula (IV) are commercially available, for example 3-aminoquinuclidine (Aldrich, dihydrochloride), (3R)-aminoquinuclidine (Aldrich, Finorga, dihydrochloride) and (3S)-aminoquinuclidine (Aldrich, dihydrochloride).

(3R)-N-methylquinuclidin-3-amine has been prepared as described in the experimental section.

Those compounds of formula (I), wherein $R_2$ is a group of formula i) and $R_5$ is an hydroxy group may also be prepared from the compounds of formula (V) by reaction with the corresponding organometallic derivative.

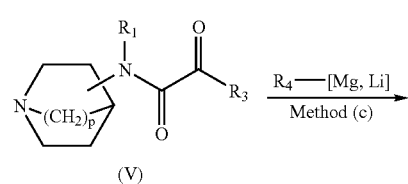

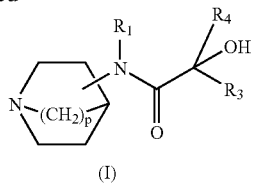

The compounds of formula (V) may be prepared from the corresponding glyoxylic acids following methods equivalent to methods (a) and (b) described in Scheme 1

Certain compounds of formula (V) are novel and fall within the scope of the present invention. In particular:
N-1-azabicyclo[2.2.2]oct-3-yl-2-oxo-2-thien-2-ylacetamide
N-[(3R)-1-Azabicyclo[2.2.2]oct-3-yl]-2-oxo-2-thien-2-ylacetamide
N-[(3S)-1-Azabicyclo[2.2.2]oct-3-yl]-2-oxo-2-thien-2-ylacetamide The quaternary ammonium derivatives of formula (II) may be prepared, as illustrated in the following scheme, by reaction of the compounds of formula (I) with an alkylating agent of formula (VI) using two possible methods -(d) or (e)-, described in detail in the experimental section. Method (e) involves the use of solid phase extraction techniques that allow the parallel preparation of several compounds.

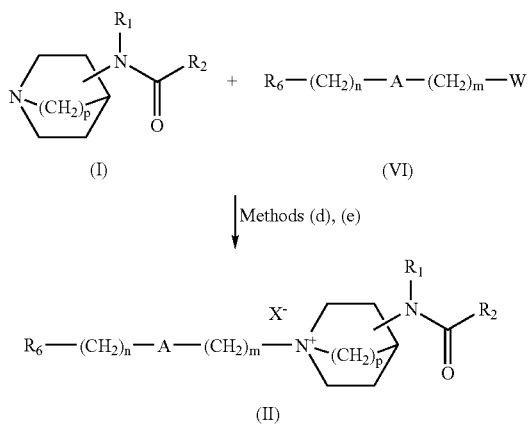

In formula (VI), W represents any suitable leaving group, preferably a group $X^{31}$ as defined above for the compounds of formula (II). When W is a leaving group other than $X^-$, the quaternary ammonium salt of formula (II) is produced from the product of method (d) or (e) by an exchange reaction according to standard methods to replace the anion W with the desired anion $X^-$.

Those compounds of general formula (VI) which are not commercially available have been prepared according to standard methods. For example, compounds wherein n=0 and A=—O—, —S—, NR' were obtained by reaction of the corresponding alcohol, thiol or amine derivative, or its sodium or potassium salt, with an alkylating agent of general formula Y—$(CH_2)_m$—W, wherein W is as defined above; most preferably W is a halogen atom and Y a halogen atom or a sulphonate ester. In other examples, compounds of general formula (VI) wherein n is at least 1 were synthesised from the corresponding alcohol derivative of general formula (VII) by methods known in the art.

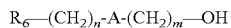

The compounds of formulae (I) and (II) can have one or more asymmetric carbons. All possible stereoisomers, single isomers and mixtures of isomers are also included within the scope of the present invention. The diastereomers of the compounds may be separated by conventional methods, for example by chromatography or crystallisation.

The structures of the compounds were confirmed by $^1$H-NMR and MS. The NMR spectra were recorded using either a Varian 300 MHz instrument or a Bruker DPX-250 instrument. Chemical shifts are expressed as parts per million ($\delta$) from the internal reference tetramethylsilane. The purity of the compounds was determined by HPLC, using reverse phase chromatography on a Waters instrument. Molecular ions were produced by electrospray ionisation mass spectrometry on a Hewlett Packard instrument.

Method (a)

Preparation of N-[(3R)-1-azabicyclo[2.2.2]oct-3-yl]-2-phenylhexanamide Example 27

2-phenylhexanoic acid was prepared by alkylation of phenylacetic acid with 1-chlorobutane following a standard method. Oxalyl chloride (0.88 ml, 0.0101 mol) was then added to a solution of 1.62 9 of 2-phenylhexanoic acid (0.0084 mol) and dimethylformamide (DMF, one drop) in 25 ml of CHCl$_3$ (ethanol free) at 0° C. The mixture was stirred and allowed to warm at room temperature. After an hour at this temperature the solvents were evaporated and the residue was dissolved in CHCl$_3$ and evaporated again. This procedure was repeated two times. The oil obtained was dissolved in CHCl$_3$ and the solution obtained cooled at 0° C. A solution of (3R)-aminoquinuclidine (1.28 g, 0.0101 mol) in CHCl$_3$ was added. The mixture was stirred and allowed to warm at room temperature. After 1 hour at this temperature, the reaction mixture was diluted with CHCl$_3$ and washed with a 10% solution of aqueous potassium-carbonate, then washed with water, dried over Na$_2$SO$_4$ and evaporated to give 3.57 g of an oil which was purified by column chromatography (silica gel, CHCl$_3$:MeOH:NH$_4$OH 90:10:1 as eluent). Appropriate fractions were combined and evaporated to give 2.42 g of a solid that after treatment with isopropyl ether yielded 1.59 g (63.1%) of the title product as a mixture of diastereomers.

mp: 136° C.

MS [M+1]$^+$: 301

$^1$H-NMR (DMSO-d6): (mixture of diastereomers 50:50) δ 0.84 (t, 3H), 1.10-1.60 (m, 9H), 1.70 (m, 1H), 1.90 (m, 1H), 2.25-2.50 (m, 1H), 2.50-2.80 (m, 4H), 2.94 & 3.05 (m, 1H), 3.50 (m, 1H), 3.65 (m, 1H), 7.15-7.40 (m, 5H), 8.04 (m, 1H, NH).

Preparation of N-[(3R)-1-Azabicyclo[2.2.2]oct-3-yl]-N-methyl-9H-xanthene-9-carboxamide Example 47

Oxalyl chloride (0.540 ml, 0.0062 mol) was added to a solution of 9H-xanthene-9-carboxylic acid (1.16 g, 0.0051 mol) and dimethylformamide (two drops) in 20 ml of CHCl$_3$ (ethanol free) at 0° C. The mixture was allowed to warm to room temperature under stirring and maintained 1 h at this temperature. After this time, the reaction mixture was concentrated to dryness in vacuo and the obtained residue was dissolved in CHCl$_3$ (15 ml) and concentrated again. This procedure was repeated two times. The obtained residue was dissolved in CHCl$_3$ and the solution cooled to 0° C. A solution of 0.865 g (0.0062 mol) of (3R)-N-methylquinuclidin-3-amine (Intermediate I-4) in 10 ml of CHCl$_3$ was added. The mixture was allowed to warm to room temperature under stirring. After 4 hours at this temperature, the reaction mixture was treated with $K_2CO_3$ (saturated solution) and the aqueous phase was extracted with $CHCl_3$. The organic solutions were combined and washed with $K_2CO_3$ (saturated solution) and water, dried over $Na_2SO_4$ filtered and concentrated to dryness. The obtained residue was purified by column chromatography (silica gel, $CHCl_3$: $NH_4OH$ 99:1→$CHCl_3$: MeOH:$NH_4OH$ 98:2:1 as eluent) to yield 900 mg (50%) of the title product.

MS [M+1]$^+$: 349

$^1$H-RMN (400 MHz, 60° C., $CDCl_3$): δ 7.26-7.19 (m, 4H), 7.10-7.01 (m, 4H), 5.51 (s, 1H), 4.18 (broad multiplet, 1H), 2.92 (s, 3H), 2.85-2.40 (m, 6H), 1.85-1.20 (m, 5H).

Preparation of (3R)-N-methylquinuclidin-3-amine (Intermediate I-4)

1 g (0.0079 mol) of (3R)-aminoquinuclidine was dissolved in 20 ml of $CH_2Cl_2$ and 1.22 ml (0.0087 mol) of triethylamine were added. The obtained solution was cooled to 0° C., $ClCO_2Et$ (0.835 ml, 0.0087 mol) was added and the mixture was stirred 15 h at room temperature. After this time, solvents were evaporated in vacuo, the obtained residue was dissolved in $CHCl_3$ and the solution washed with $K_2CO_3$ (saturated solution) and water. The organic phase was dried over $Na_2SO_4$, filtered and concentrated to dryness. The obtained residue was used without further purification as is described as follows. The obtained residue was dissolved in 15 ml of THF, the solution was cooled to 0° C. and 0.601 g (0.016 mol) of $LiAlH_4$ were added in several portions. The reaction mixture was heated under reflux for 4 h. After this time, was cooled to 0° C. and the excess of hydride was decomposed by the consecutive addition, under stirring, dropwise and cautiously of 0.6 ml of $H_2O$, 0.6 ml of NaOH (10% solution) and 1.8 ml of $H_2O$. When the decomposition was finished, the reaction mixture was filtered and the sludge was washed with THF and $CHCl_3$, the organic solutions were combined and concentrated to dryness to obtain 830 mg (75%) of the title product, structure confirmed by $^1$H-RMN and $^{13}$C-RMN.

$^{13}$C-RMN ($CDCl_3$): δ 57.0 (CH), 56.5 (CH2), 47.5 (CH2), 46.9 (CH2), 34.3 (CH3), 26.1 (CH2), 24.6 (CH), 19.9 (CH2).

The following Examples of formula (I) were prepared by method (a) from the appropriate carboxylic acid:

N-[(3R)-1-Azabicyclo[2.2.2]oct-3-yl]-2,3-diphenylpropanamide (Example 25) from 2,3-diphenylpropionic acid.

N-1-Azabicyclo[2.2.2]oct-3-yl)-9H-xanthene-9-carboxamide (Example 28)

N-[(3R)-1-Azabicyclo[2.2.2]oct-3-yl]-9H-xanthene-9-carboxamide (Example 31)

N-[(3S)-1-Azabicyclo[2.2.2]oct-3-yl]-9H-xanthene-9-carboxamide (Example 33)

All three from 9H-xanthene-9 carboxylic acid.

Method (b)

Preparation of N-[(3R)-1-azabicyclo[2.2.2]oct-3-yl]-2,2-dithien-2-ylacetamide Example 17

2,2-dithien-2-ylacetic acid was produced by hydrolysis of 2,2-dithien-2-ylacetic acid methyl ester, previously prepared as described in F. Leonard and 1. Ehranthal, *J. Am. Chem. Soc,* (1951), Vol 73, pag 2216. 1.2 g (0.0054 mol) of 2,2-dithien-2-ylacetic acid were dissolved in 25 ml of THF. To this solution were added 0.96 g (0.00594 mol) of 1,1'-carbonyldiimidazole and the mixture was refluxed for an hour. The reaction was monitored by TLC following the formation of the imidazolide. When the reaction was completed 0.75 g (0.00594 mol) of (3R)-aminoquinuclidine were added. The reaction mixture was refluxed for 16 h, cooled, diluted with ether and washed with water. The organic layer was extracted with HCl 2N, the acid solution basified with $K_2CO_3$ and extracted with $CHCl_3$. The organic phase was dried over $Na_2SO_4$ and the solvent was evaporated to obtain 0.60 g of an oil which was purified by column chromatography (silica gel, $CHCl_3$: MeOH:$NH_4OH$ 90:10:1 as eluent). Appropriate fractions were combined and evaporated to give 0.31 g of the title product (17.3%).

mp: 165° C.

MS [M+1]$^+$: 333

$^1$H-NMR ($CDCl_3$): δ 1.43 (m, 2H), 1.63 (m, 2H), 1.92 (m, 1H), 2.4 (m, 1H), 2.65-2.85 (m, 4H), 3.31 (m, 1H), 3.97 (m, 1H), 5.37 (s, 1H), 5.98 (d, 1H, NH), 7.0 (m, 4H), 7.28 (m, 2H).

Preparation of N-[(3R)-1-Azabicyclo[2.2.2]oct-3-yl]-9-hydroxy-9H-fluorene-9-carboxamide Example 44

5 g (0.022 mol) of 9-hydroxy-9H-fluorene-9-carboxylic acid were dissolved in 50 ml of dry DMF and 4.2 g (0.026 mol) of 1,1'-carbonyldiimidazole were added. The mixture was stirred during 1 h at room temperature. After this time 3.26 g (0.026 mol) of (3R)-aminoquinuclidine and 0.324 g (0.0027 mol) of DMAP (4-(dimethylamino)pyridine) were added. The reaction mixture was stirred at room temperature during 14 hours, then was concentrated in vacuo to eliminate the DMF and the obtained residue was dissolved in AcOEt. The organic solution was washed with $NaHCO_3$ (saturated solution) and water. The organic layer was separated, dried over $Na_2SO_4$ and solvent was evaporated. The obtained product was purified by column chromatography (silica gel, $CHCl_3$: $NH_4OH$ 100:1→$CHCl_3$: MeOH:$NH_4OH$ 80:20:1 as eluent). Appropriate fractions were combined and evaporated to yield 304 mg of the title product (4%).

MS [M+1]$^+$: 335

$^1$H-RMN ($CDCl_3$): δ 7.67-7.62 (m, 2H), 7.42-7.36 (m, 4H), 7.32-7.25 (m, 2H), 6.08-5.93 (m, NH, 1H), 3.74 (m, 1H), 3.00-2.87 (m, 1H), 2.52-2.27 (m, 4H), 2.02-1.92 (m, 1H), 1.80-1.76 (m, 1H), 1.51-1.44 (m, 2H), 1.26-1.17 (m, 2H).

Preparation of (2S)-N-[(3R)-1-azabicyclo[2.2.2]oct-3-yl]-2-cyclopentyl-2-hydroxy-2-thien-2-ylacetamide Example 49

The title compound was prepared as is described in Example 44 starting from (2S)-2-Cyclopentyl-2-hydroxy-2-thien-2-yl acetic acid. The obtained product was purified by column chromatography (silica gel, $CHCl_3$:MeOH:$NH_4OH$ 99:1:1→$CHCl_3$: MeOH:$NH_4OH$ 97:3:1 as eluent) to give 800 mg of the title product impurified with imidazole. The obtained product was dissolved in $CHCl_3$ and washed with $H_2O$ (×3). The organic solution was dried over $Na_2SO_4$, filtered and concentrated in vacuo to yield 650 mg of the title product (44% from the starting acid). Structure confirmed by $^1$H-RMN and MS.

MS [M+1]$^+$: 335

$^1$H-RMN ($CDCl_3$): δ 7.24 (m, 1H), 7.08 (m, 1H), 6.97 (m, 1H), 6.64 (d, NH, 1H), 3.91-3.81 (m, 1H), 3.33-3.23 (m, 1H), 2.88-2.69 (m, 5H), 2.42-2.33 (m, 1H), 1.87 (m, 1H), 1.69-1.36 (m, 12H)

(2S)-2-Cyclopentyl-2-hydroxy-2-thien-2-yl acetic acid has been prepared as is described in WO02/053564

The following Examples of formula (I) were prepared according to method (b) from the appropriate carboxylic acid:

N-[(3R)-1-Azabicyclo[2.2.2]oct-3-yl]-2-cyclopentyl-2-hydroxy-2-thien-2-ylacetamide (Example 19) from 2-cyclopentyl-2-hydroxy-2-thien-2-ylacetic acid, which was produced by hydrolysis of 2-cyclopentyl-2-hydroxy-2-thien-2-ylacetic acid methyl ester, compound described in E. Atkinson et al., *J. Med. Chem.*, (1977), Vol 20, no 12, 1612-1617 and WO02/053564.

N-[(3R)-1-Azabicyclo[2.2.2]oct-3-yl]-2-cyclopentyl-2-hydroxy-2-phenylacetamide (Example 26) from 2-cyclopentyl-2-hydroxy-2-phenylacetic acid.

N-(1-Azabicyclo[2.2.2]oct-3-yl)-9H-xanthene-9-carboxamide (Example 28) from 9H-xanthene-9 carboxylic acid N-(1-Azabicyclo[2.2.2]oct-3-yl)-9-hydroxy-9H-fluorene-9-carboxamide (Example 41) from 9-Hydroxy-9H-fluorene-9-carboxylic acid.

Method (c)

Preparation of N-[(3R)-1-azabicyclo[2.2.2]oct-3-yl]-2-oxo-2-thien-2-ylacetamide (Intermediate I-1)

Oxalyl chloride (4.5 ml, 0.0516 mol) was added to a solution of 6.68 g (0.0428 mol) of 2-oxo-2-thien-2-ylacetic acid and DMF (several drops) in 100 ml of $CHCl_3$ (ethanol free) at 0° C. The mixture was stirred and allowed to warm to room temperature. After two hours at this temperature, the solvents were evaporated and the residue was dissolved in $CHCl_3$ and evaporated again. This procedure was repeated two times. The oil obtained was dissolved in $CHCl_3$ and the solution obtained cooled at 0° C. A solution of (3R)-aminoquinuclidine (5.91g, 0.0468 mol) in 50 ml of $CHCl_3$ was added. The mixture was stirred and allowed to warm to room temperature. After 18 hours at this temperature, the reaction mixture was washed with an aqueous $K_2CO_3$ solution. The basic aqueous solution was extracted again with $CHCl_3$. The organic phases were combined, washed with water, dried over $Na_2SO_4$ and evaporated to give 11.34 g of the title product.

MS [M+1]$^+$: 265

$^1$H-NMR ($CDCl_3$): δ 1.40-1.85 (m, 4H), 2.0 (m, $_1$H), 2.60 (m,1H), 2.70-3.0 (m, 4H), 3.4 (m, 1H), 4.0 (m, 1H), 7.20 (m, 1H), 7.50 (d,$_1$H, NH), 7.85 (m, 1H), 8.40 (m, 1H).

Following an equivalent procedure the following intermediates were prepared:

N-[(3S)-1-Azabicyclo[2.2.2]oct-3-yl]-2-oxo-2-thien-2-ylacetamide (Intermediate I-2)

N-1-Azabicyclo[2.2.2]oct-3-yl]-2-oxo-2-thien-2-ylacetamide (Intermediate I-3)

Preparation of N-[(3R)-1-azabicyclo[2.2.2]oct-3-yl]-2-hydroxy-2,2-dithien-2-yl-acetamide Example 4

A solution of 2-thienylmagnesium bromide was prepared from 2.27 g (0.094 mol) of magnesium and 15.4 g (0.094 mol) of 2-bromothiophene in 150 ml of THF. This solution was added to a solution of 11.34 g (0.043 mol) of N-[(3R)-1-azabicyclo[2.2.2]oct-3-yl]-2-oxo-2-thien-2-ylacetamide (Intermediate I-1) in 120 ml of THF. The mixture was stirred at room temperature for one hour, refluxed for one hour, cooled and treated with a saturated solution of ammonium chloride. The solution obtained was basified with a $K_2CO_3$ solution and extracted with $CH_2Cl_2$. The organic layer was washed with water and brine, dried over $Na_2SO_4$ and treated with activated carbon. The solution obtained was filtered trough Celite and solvents were evaporated to give a solid that was treated with ether and filtered to give 8.77 (58.5%) of the title product.

m. p.: 169° C.

MS [M+1]$^+$: 349

$^1$H-NMR (DMSO-d$_6$): δ 1.30 (m, 1H), 1.42-1.75 (m, 3H), 1.77 (m, 1H), 2.50-2.75 (m, 4H), 2.83 (m, 1H), 3.05 (m, 1H), 3.74 (m, 1H), 6.95 (m, 2H), 7.03 (m, 1H), 7.09 (m, 1H), 7.43 (m, 2H), 7.54 (s,1H, OH), 7.97 (d, 1H, NH).

The following Examples of formula (I) were prepared according to method (c) using N-[(3R)-1-azabicyclo[2.2.2] oct-3-yl]-2-oxo-2-thien-2-ylacetamide (Intermediate I-1) and the corresponding Grignard reagent:

N-[(3R)-1-Azabicyclo[2.2.2]oct-3-yl]-2-hydroxy-2-thien-2-ylpent4-enamide (Example 20).

(2*)-N-[(3R)-1-Azabicyclo[2.2.2]oct-3-yl]-2-hydroxy-2-thien-2-ylbutanamide (diastereomer 1, Example 21) and (2*)-N-[(3R)-1-Azabicyclo[2.2.2]oct-3-yl]-2-hydroxy-2-thien-2-ylbutanamide (diastereomer 2, Example 22) the two diastereomers were separated by column chromatography (silica gel, $CHCl_3$/MeOH/$NH_4OH$ 90:10:1 as eluent). Diastereomer 1: first diastereomer obtained, Diastereomer 2: second distereomer obtained.

(2*)-N-[(3R)-1-Azabicyclo[2.2.2]oct-3-yl]-2-hydroxy-2-thien-2-ylbut-3-enamide (diastereomer 1, Example 23) and (2*)-N-[(3R)-1-Azabicyclo[2.2.2]oct-3-yl]-2-hydroxy-2-thien-2-ylbut-3-enamide (diastereomer 2, Example 24) the two diastereomers were separated by column chromatography (silica gel, $CHCl_3$/MeOH/$NH_4OH$ 90:10:1 as eluent). Diastereomer 1: first diastereomer obtained, Diastereomer 2: second distereomer obtained.

(*) Configuration not assigned.

The following compounds of formula (I) were also prepared according to method (c)

N-[(3S)-1-Azabicyclo[2.2.2]oct-3-yl]-2-hydroxy-2,2-dithien-2-ylacetamide (Example 15) prepared from Intermediate I-2 and 2-thienyllithium (commercially available).

N-(1-Azabicyclo[2.2.2]oct-3-yl)-2-hydroxy-2,2-dithien-2-ylacetamide (Example 1) prepared from Intermediate I-3 and 2-thienyllithium.

Preparation of N-[(3R)-1-Azabicyclo[2.2.2]oct-3-yl]-2-(5-bromothien-2-yl)-2-(4-fluoro-3-methylphenyl)-2-hydroxyacetamide (Example 48)

Oxalyl chloride (1.16 ml, 0.013 mol) was added to a suspension of 2-(5bromothien-2-yl)-2-oxoacetic acid (2.6 g, 0.011 mol) and two drops of DMF in 30 ml of $CHCl_3$ (ethanol free) cooled to 0° C. The mixture was allowed to warm to room temperature under stirring. After 1.5 hours the reaction mixture was concentrated to dryness in vacuo and the obtained residue was dissolved in $CHCl_3$ (15 ml) and concentrated again. This procedure was repeated two times. The obtained residue was dissolved in $CHCl_3$ (30 ml), the solution was cooled to 0° C and 1.67 g (0.013 mol) of (3R)-aminoquinuclidine were added. The mixture was allowed to warm to room temperature and continued stirring during 3 hours. After this time the reaction mixture was treated with $K_2CO_3$ (saturated solution) and the aqueous layer was extracted with $CH_2Cl_2$. The organic layers were combined, washed with water, dried over $Na_2SO_4$, filtered and evaporated. The obtained product (N-[(3R)-1-azabicyclo[2.2.2]oct-3-yl]-2-(5-bromothien-2-yl)-2-oxoacetamide) was used without further purification as is described as follows. The obtained product was dissolved in dry THF (45 ml). The solution obtained was cooled to −80° C. and 14.4 ml of a 1M solution in THF of 4-fluoro-3-methylphenylmagnesium bromide (0.014 mol) were added. The mixture was stirred during 3 hours at low temperature. After this time, the reaction mixture was treated with $NH_4Cl$ (saturated solution) and extracted with AcOEt. The organic layer was dried over $Na_2SO_4$, filtered and solvents were evaporated. The obtained product was purified by column chromatography (silica gel, CHCl$_3$:MeOH:NH$_4$OH 99:1:1→CHCl$_3$:MeOH:NH$_4$OH 96:4:1) to yield 2.1 g of the title compound (42% from the starting acid) as a mixture of diastereomers.

MS [M+1]$^+$: 453, 455

$^1$H-RMN (CDCl$_3$): (mixture of diastereomers) δ 7.35-7.20 (m, 2H), 7.08-6.89 (m, 3H), 6.80 (dd, 1H), 3.93-3.84 (m, 1H), 3.18-3.07 (m, 1H), 2.69-2.58 (m, 4H), 2.33-2.22 (m, 4H), 1.92-1.87 (m, 1H), 1.63-1.42 (m, 4H)

2-(5-bromothien-2-yl)-2-oxoacetic acid was obtained by hydrolysis of ethyl 2-(5-bromothien-2-yl)-2-oxoacetate by a standard method (EtOH, NaOH 2N, 60° C., 1.5 h).

Preparation of N-[(3R)-1-Azabicyclo[2.2.2]oct-3-yl]-2-fur-2-yl-2-hydroxypent-3-ynamide Example 45

To a suspension cooled to 0° C. of 1.72 g (0.012 mol) of 2-fur-2-yl-2-oxoacetic acid and two drops of DMF in 40 ml of CHCl$_3$ (ethanol free), 1.17 ml (0.013 mol) of oxalyl chloride were added. The resulting mixture was allowed to warm to room temperature under stirring and continued stirring during 1 hour. After this time, the mixture was concentrated to dryness in vacuo and the obtained residue was dissolved in CHCl$_3$ (20 ml) and concentrated again. This procedure was repeated two times. The obtained product was dissolved in CHCl$_3$ (50 ml), the solution was cooled to 0° C. and 1.7 g (0.013 mol) of (3R)-aminoquinuclidine were added. The mixture was allowed to warm to room temperature and continued stirring during 16 hours. After this time the reaction mixture was treated with K$_2$CO$_3$ (saturated solution) and the aqueous layer was extracted with CH$_2$Cl$_2$. The organic layers were combined, washed with water, dried over Na$_2$SO$_4$, filtered and evaporated. The obtained product (N-[(3R)-1-azabicyclo[2.2.2]oct-3-yl]-2-(2-furyl)-2-oxoacetamide) was used without further purification as is described as follows. This product was dissolved in dry THF (50 ml). The solution obtained was cooled to –0° C. and 28 ml of a 0.5 M solution in THF of 1-propynylmagnesium bromide (0.014 mol) were added. The mixture was allowed to warm to room temperature during 3 hours. After this time, the reaction mixture was treated with NH$_4$Cl (saturated solution) and extracted with AcOEt and CH$_2$Cl$_2$. The organic layers were combined, dried over Na$_2$SO$_4$, filtered and solvents were evaporated. The obtained product was purified by column chromatography (silica gel, CHCl$_3$:MeOH:NH$_4$OH 97:3:1→CHCl$_3$:MeOH:NH$_4$OH 94:6:1 as eluent) to yield 1.38 g of the title compound (39% from the starting acid) as a mixture of diastereomers.

MS [M+1]$^+$: 289

$^1$H-RMN (CDCl$_3$): (mixture of diastereomers) δ 7.36-7.35 (m, $_1$H), 6.87-6.76 (m, NH, 1H), 6.54-6.52 (m, 1H), 6.34-6.32 (m, 1H), 3.92 (m, 1H), 3.29-3.17 (m, 1H), 2.78-2.64 (m, 4H), 2.47-2.35 (m, 1H), 2.00-1.90 (m, 1H), 1.92 (s, 3H), 1.70-1.39 (m, 4H).

Preparation of N-[(3R)-1-Azabicyclo[2.2.2]oct-3-yl]-2-fur-2-yl-2-hydroxy-4-(4-methoxyphenyl)butanamide (Example 46)

This product was prepared according to the procedure described in Example 45, starting from 2 g (0.014 mol) of 2-fur-2-yl-2-oxoacetic acid, and using 4-methoxyphenylethyl-magnesium chloride (0.021 mol, 43 ml of a 0.5 M solution in THF) as Grignard reagent. The obtained product was purified by column chromatography (silica gel, CHCl$_3$:MeOH:NH$_4$OH 99:1:1→CHCl$_3$:MeOH:NH$_4$OH 97:3:1 as eluent) to yield 2.4 g of the title compound (44% from the starting acid) as a mixture of diastereomers.

MS [M+1]$^+$: 385

$^1$H-RMN (CDCl$_3$): (mixture of diastereomers) δ 7.39-7.38 (m, 1H), 7.09 (d, 2H), 6.82 (d, 2H), 6.70-6.67 (m, NH, 1H), 6.41-6.35 (m, 2H), 3.92 (m, 1H), 3.78 (s, 3H), 3.33-3.24 (m, 1H), 2.82-2.19 (m, 9H), 1.96-1.87 (m, 1H), 1.67-1.40 (m, 4H)

Method (d)

Preparation of (3R)-1-(3-phenoxypropyl)-3-[(9H-xanthen-9-ylcarbonyl)amino]-1-azoniabicyclo[2.2.2] octane bromide (Example 32)

0.3 g (0.00089 mol) of N-[(3R)-1-azabicyclo[2.2.2]oct-3-yl]-9H-xanthene-9-carboxamide (Example 31) were dissolved in 6 ml of THF. To this solution 0.21 ml (0.287 g, 0.001335 mol) of (3-bromopropoxy)benzene were added. The mixture was refluxed during 4 hours and then stirred 17 h at room temperature. The reaction mixture was filtered and the solid obtained washed with ether several times and dried. 0.48 g (98%) of the title product were obtained.

m.p.: 278.5-279.2° C.

MS [M-Br]$^+$: 469

$^1$H-NMR (DMSO-d$_6$): δ 1.80-2.0 (m, 3H), 2.05-2.30 (m, 4H), 3.15-3.25 (m, 1H), 3.30-3.65 (m, 6H), 3.82 (m, 1H), 4.05 (t, 2H), 4.10 (m, 1H), 5.05 (s, 1H), 6.90-7.0 (m, 3H), 7.05-7.20 (m, 4H), 7.25-7.42 (m, 6H), 9.01 (d, 1H, NH).

Preparation of 3-{[(9-hydroxy-9H-fluoren-9-yl)carbonyl]amino}-1-methyl-1-azoniabicyclo[2.2.2]octane bromide (Example 42)

0.245 g (0.00073 mol) of N-(1-azabicyclo[2.2.2]oct-3-yl)-9-hydroxy-9H-fluorene-9-carboxamide (Example 41) were dissolved in 4 ml of acetonitrile and 6 ml of CHCl$_3$. To this solution 5.46 ml of a 1 M solution of methyl bromide in acetonitrile were added and the mixture was stirred for 96 h at room temperature under N$_2$ atmosphere. After this time the solvents were evaporated. The residue was coevaporated with ether three times. Ether was added to the residue and the mixture stirred. The solid obtained was filtered and washed several times with ether. The yield was 0.26 g (83.8%) of the title compound.

m.p.: 197.5-203.6° C.

MS [M-Br]$^+$: 349

$^1$H-NMR (DMSO-d$_6$): δ 1.80-2.0 (m, 3H), 2.10-2.25 (m, 2H), 2.96 (s, 3H), 3.35-3.70 (m, 5H), 3.78 (m, 1H), 4.15 (m, 1H), 6.82 (s, 1H, OH), 7.30 (m, 2H), 7.43 (m, 4H), 7.79 (m, 2H), 8.81 (d, 1H, NH).

Method (e)

Preparation of (3S)-1-cyclohexylmethyl-3-[(9H-xanthen-9-ylcarbonyl)amino]-1-azoniabicyclo[2.2.2] octane trifluoroacetate (Example 36)

28.15 mg (0.0842 mmol) of N-[(3S)-1-azabicyclo[2.2.2] oct-3-yl]-9H-xanthene-9-carboxamide (Example 33) were dissolved in 0.5 ml of DMSO. A solution of 74.37 mg (0.421 mmol) of (bromomethyl)cyclohexane in 0.5 ml of DMSO was added and the mixture stirred at room temperature overnight. The mixture was purified by solid phase extraction with a cation exchange Mega Bond Elut cartridge, previously conditioned at pH=7.5 with 0.1 M NaH$_2$PO$_4$ buffer. The reaction mixture was applied to the cartridge and washed first with 2 ml of DMSO and then three times with 5 ml of acetonitrile, rinsing away all starting materials. The ammonium derivative was eluted with 5 ml of 0.03 M TFA solution in CH$_3$CN: CHCl$_3$ (2:1). This solution was neutralized with 300 mg of poly(4-vinylpyridine), filtered and evaporated to dryness. The yield was 12.4 mg of the title product. (27.0%).

[M-CF$_3$COO]$^+$: 431

Preparation of (3R)-3-(2-hydroxy-2,2-dithien-2-ylacetylamino)-1-[3-(3-hydroxyphenoxy)propyl]-1-azoniabicyclo[2.2.2]octane trifluoroacetate (Example 12)

The title compound was prepared as described for Example 36 from 30 mg (0.0861 mmol) of N-[(3R)-1-azabicyclo[2.2.2]oct-3-yl]-2-hydroxy-2,2-dithien-2-ylacetamide (Example 4) (dissolved in 0.5 ml of DMSO) and 78 mg (0.418 mmol) of 3-(3-chloropropoxy)phenol (dissolved in 0.5 ml of DMSO). The yield was 12.7 mg of the title product. (24%).

[M-CF$_3$COO]$^+$: 499

Also included within the scope of the present invention are pharmaceutical compositions which comprise, as the active ingredient, at least one quinuclidine amide derivative of formulae (I) or (II) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 1 and 500 mg, preferably from 5 to 300 mg of active ingredient. The inhalant compositions may contain between 1 μg and 1,000 μg, preferably from 10 μg to 800 μg of active ingredient. In human therapy, the dose of the compound of formulae (I) or (II) depend on the desired effect and duration of treatment; adult doses are generally between 3 mg and 300 mg per day as tablets and 10 μg and 800 μg per day as inhalant composition.

Pharmacological Action

The results on human muscarinic receptors binding and in the test on bronchospasm in guinea pig, were obtained as described below.

Human Muscarinic Receptor Studies.

The binding of [3H]-NMS to human muscarinic receptors was performed according to Waelbroeck et al (1990), Mol. Pharmacol., 38: 267-273. Assays were carried out at 25° C. Membrane preparations from stably transfected chinese hamster ovary-K1 cells (CHO) expressing the genes for the human M3 muscarinic receptors were used.

For determination of IC$_{50}$, membrane preparations were suspended in DPBS to a final concentration of 89 μg/ml for the M3 subtype. The membrane suspension was incubated with the tritiated compound for 60 min. After incubation the membrane fraction was separated by filtration and the bound radioactivity determined. Non-specific binding was determined by addition of 10$^{-4}$ M atropine. At least six concentrations were assayed in duplicate to generate individual displacement curves.

Our results show that the compounds of the present invention have high affinities for M3 muscarinic receptors, preferably human muscarinic receptors. Thus, the IC$_{50}$ of the preferred compounds of the invention is lower than 100 nM. Most preferred compounds, such as the compounds of examples 1, 3, 4, 8, 10, 11, 14, 19, 30 and 32 described below, have an IC$_{50}$ lower than 60 nM.

Test on Bronchospasm in Guinea Pig

The studies were performed according to H. Konzett and F. Rössler (1940), Arch. Exp. Path. Pharmacol. 195: 71-74. Aqueous solutions of the agents to be tested were nebulized and inhaled by anaesthetized ventilated male guinea pigs (Dunkin-Hartley). Bronchial response to intravenous acetylcholine challenge was determined before and after drug administration and the changes in pulmonary resistance at several time-points were expressed as percent of inhibition of bronchospasm.

The compounds of the present invention inhibited the bronchospasm response to acetylcholine with high potency and a long duration of action.

From the above described results one of ordinary skill in the art can readily understand that the compounds of the present invention have excellent M3 antimuscarinic activity and thus are useful for the treatment of diseases in which the M3 muscarinic receptor is implicated, including respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia.

The present invention further provides a compound of formulae (I) or (II) or a pharmaceutically acceptable composition comprising a compound of formulae (I) or (II) for use in a method of treatment of the human or animal body by therapy, in particular for the treatment of respiratory, urological or gastrointestinal disease or disorder.

The present invention further provides the use of a compound of formulae (I) or (II) or a pharmaceutically acceptable composition comprising a compound of formulae (I) or (II) for the manufacture of a medicament for the treatment of a respiratory, urological or gastrointestinal disease or disorder.

Further, the compounds of formulae (I) or (II) and pharmaceutical compositions comprising a compound of formulae (I) or (II) can be used in a method of treating a respiratory, urological or gastrointestinal disease or disorder, which method comprises administering to a human or animal patient in need of such treatment an effective, non-toxic amount of a compound of formulae (I) or (II) or a pharmaceutical composition comprising a compound of formulae (I) or (II).

Further, the compounds of formulae (I) or (II) and pharmaceutical compositions comprising a compound of formulae (I) or (II) can be used in combination with other drugs effective in the treatment of these diseases. For example with β$_2$ agonists, steroids, antiallergic drugs, phosphodiesterase IV inhibitors and/or-leukotriene D4 (LTD4) inhibitors, for simultaneous, separate or sequential use in the treatment of a respiratory disease.

The present invention will be further illustrated by the following examples. The examples are given by way of illustration only and are not to be construed as a limiting.

EXAMPLE 1

N-(1-Azabicyclo[2.2.2]oct-3-yl)-2-hydroxy-2,2-dithien-2-ylacetamide

The title compound was synthesised according to method c. The yield was 0.67 9, 15.2%.

m.p.: 185° C.
MS [M+1]$^+$: 349.
$^1$H-NMR (DMSO-d$_6$): δ 1.30 (m,$_1$H), 1.40-1.75 (m, 3H), 1.77 (m, 1H), 2.50-2.75 (m, 4H), 2.83 (m, 1H), 3.05 (m, 1H), 3.74 (m, 1H), 6.94 (m, 2H), 7.04 (m, 1H), 7.10 (m, 1H), 7.43 (m, 2H), 7.53 (s, 1H, OH), 7.95 (d, 1H, NH).

EXAMPLE 2

3-(2-Hydroxy-2,2-dithien-2-ylacetylamino)-1-methyl-1-azoniabicyclo[2.2.2]octane bromide The title compound was synthesised according to methods c and d. The yield of the final step was 0.16 g, 68%.

MS [M-Br]$^+$: 363.
$^1$H-NMR (DMSO-d$_6$): δ 1.76 (m, 1H), 1.85-2.08 (m, 3H), 2.14 (m,$_1$ H), 2.92 (s, 3H), 3.30-3.60 (m, 5H), 3.75 (m, 1H), 4.20 (s, 1H), 7.0 (m, 2H), 7.06 (m, 1H), 7.12 (m, 1H), 7.46 (m, 2H), 7.65 (s, 1H, OH), 8.64 (d, 1H, NH).

EXAMPLE 3

3-(2-Hydroxy-2,2-dithien-2-ylacetylamino)-1-3-phenoxypropyl)-1-azoniabicyclo[2.2.2]octane bromide The title compound was synthesised according to methods c and d. The yield of the final step was 0.24 g, 82.7%.

m.p.:180.6-188.3° C.
MS [M-Br]$^+$: 483.
$^1$H-NMR (DMSO-d$_6$): δ 1.78 (m,$_1$H), 1.90-2.25 (m, 6H), 3.30-3.65 (m, 7H), 3.67-3.80 (m, 1H), 4.05 (t, 2H), 4.24 (m, $_1$H), 6.94-7.0 (m, 5H), 7.07 (m, 1H), 7.13 (m, 2H), 7.47 (m, 2H), 7.66 (s, 1H, OH), 8.74 (d, 1H, NH).

EXAMPLE 4

N-[(3R)-1-Azabicyclo[2.2.2]oct-3-yl]-2-hydroxy-2,2-dithien-2-ylacetamide

The title compound was synthesised according to method c. The yield was 8.77 g, 58.5%.

m.p.: 169° C.
MS [M+1]$^+$: 349.
$^1$H-NMR (DMSO-d$_6$): δ 1.30 (m, 1H), 1.42-1.75 (m, 3H), 1.77 (m, 1H), 2.50-2.75 (m, 4H), 2.83 (m, $_1$H), 3.05 (m, 1H), 3.74 (m, 1H), 6.95 (m, 2H), 7.03 (m, 1H), 7.09 (m, 1H), 7.43 (m, 2H), 7.54 (s, 1H, OH), 7.97 (d, 1H, NH).

EXAMPLE 5

(3R)-3-2-Hydroxy-2,2-dithien-2-ylacetylamino)-1-methyl-1-azoniabicyclo[2.2.2]octane trifluoroacetate The title compound was synthesised according to methods c and e. The yield of the final step was 0.0124 g, 30.2%.

MS [M-CF$_3$COO]$^+$: 363.

EXAMPLE 6

(3R)-1-Allyl-3-(2-hydroxy-2,2-dithien-2-ylacetylamino)-1-azoniabicyclo[2.2.2]octane trifluoroacetate The title compound was synthesised according to methods c and e. The yield of the final step was0.010g, 23.1%.

MS [M-CF$_3$COO]$^+$: 389.

EXAMPLE 7

(3R)-1-Heptyl-3-(2-hydroxy-2,2-dithien-2-ylacetylamino)-1-azoniabicyclo[2.2.2]octane trifluoroacetate The title compound was synthesised according to methods c and e. The yield of the final step was 0.0118 9, 24.4%.

MS [M-CF$_3$COO]$^+$: 447.

EXAMPLE 8

(3R)-3-2-Hydroxy-2,2-dithien-2-ylacetylamino)-1-(3-phenylpropyl)-1-azoniabicyclo[2.2.2]octane bromide The title compound was synthesised according to methods c and d. The yield of the final step was 0.49 g, 78%.

m.p.: 117.3-118.9° C.
MS [M-Br]$^+$: 467
$^1$H-NMR (DMSO-d$_6$): δ 1.75 (m,1H), 1.80-2.05 (m, 5H), 2.09 (m, 1H), 2.60 (m, 2H), 3.16 (m, 2H), 3.25-3.60 (m, 5H), 3.68 (m, 1H), 4.21 (m, 1H), 6.96 (m, 2H), 7.04 (m, 1H), 7.11 (m, 1H), 7.20-7.40 (m, 5H), 7.45 (m, 2H), 7.62 (s, 1H, OH), 8.70 (d, 1H, NH).

EXAMPLE 9

(3R)-3-(2-Hydroxy-2,2-dithien-2-ylacetylamino)-1-((E)-3-phenylallyl)-1-azoniabicyclo[2.2.2]octane trifluoroacetate The title compound was synthesised according to methods c and e. The yield of the final step was 0.0032 g, 6.4%.

[M-CF$_3$COO]$^+$: 465.

EXAMPLE 10

(3R)-3-(2-Hydroxy-2,2-dithien-2-ylacetylamino)-1-(2-phenoxyethyl)-1-azoniabicyclo[2.2.2]octane bromide The title compound was synthesised according to methods c and d. The yield of the final step was 0.470 g, 74%.

m.p.: 112.6-113.9° C.
MS [M-Br]$^+$: 469
$^1$H-NMR (DMSO-d$_6$): δ 1.77 (m, 1H), 1.90-2.15 (m, 4H), 3.40-3.80 (m, 7H), 3.86 (m, 1H), 4.24 (m, 1H), 4.43 (m, 2H), 6.95-7.0 (m, 5H), 7.04 (m, 1H), 7.11 (m, 1H), 7.35 (m, 2H), 7.46 (m, 2H), 7.66 (s, 1H, OH), 8.72 (d, 1H, NH).

EXAMPLE 11

(3R)-3-(2-Hydroxy-2,2-dithien-2-ylacetylamino)-1-(3-phenoxypropyl)-1-azoniabicyclo[2.2.2]octane bromide The title compound was synthesised according to methods c and d. The yield of the final step was 0.65 9, 80%.

m.p.: 182° C.

MS [M-Br]$^+$: 483

$^1$H-NMR (DMSO-d$_6$): δ 1.76 (m, 1H), 1.85-2.25 (m, 6H), 3.25-3.65 (m, 7H), 3.65-3.82 (m, 1H), 4.05 (t, 2H), 4.23 (m, 1H), 6.90-7.0 (m, 5H), 7.04 (m, 1H), 7.11 (m, 1H), 7.31 (m, 2H), 7.45 (m, 2H), 7.65 (s, 1H, OH), 8.73 (d, 1H, NH).

EXAMPLE 12

(3R)-3-(2-Hydroxy-2,2dithien-2-ylacetylamino)-1-[3-(3-hydroxyphenoxy)propyl]-1-azoniabicyclo[2.2.2]octane trifluoroacetate The title compound was synthesised according to methods c and e. The yield of the final step was 0.0127 9, 24.0%.

[M-CF$_3$COO]$^+$: 499.

EXAMPLE 13

(3R)-1-(2-Benzyloxyethyl)-3-(2-hydroxy-2,2-dithien-2-ylacetylamino)-1-azoniabicyclo[2.2.2]octane trifluoroacetate The title compound was synthesised according to methods c and e. The yield of the final step was 0.0146 9, 28.4%.

[M-CF$_3$COO]$^+$: 483.

EXAMPLE 14

(3R)-3-(2-Hydroxy-2,2dithien-2-ylacetylamino)-1-(3-thien-2-ylpropyl)-1-azoniabicyclo[2.2.2]octane bromide The title compound was synthesised according to methods c and d. The yield of the final step was 0.49 g, 77%.

m.p.: 111.1-113.2° C.

MS [M-Br]$^+$: 473

$^1$H-NMR (DMSO-d$_6$): δ 1.75 (m, 1H), 1.85-2.15 (m, 6H), 2.84 (t, 2H), 3.17 (m, 2H), 3.25-3.45 (m, 3H), 3.45-3.62 (m, 2H), 3.70 (m, 1H), 4.21 (m, 1H), 6.90-7.0 (m, 4H), 7.05 (m, 1H), 7.11 (m, 1H), 7.38 (m, 1H), 7.45 (m, 2H), 7.65 (s, 1H, OH), 8.71 (d, 1H, NH).

EXAMPLE 15

N-[(3S)-1-Azabicyclo[2.2.2]oct-3-yl]-2-hydroxy-2,2-dithien-2-ylacetamide

The title compound was synthesised according to method c. The yield was 0.44 g, 7.67%.

MS [M+1]$^+$: 349.

$^1$H-NMR (CDCl$_3$): δ 1.40-1.70 (m, 4H), 1.98 (m,$_1$ H), 2.40-2.47 (m, 1H), 2.60-2.85 (m, 4H), 3.24 (m, 1H), 3.97 (m, 1H), 6.91 (d, 1H), 7.01 (m, 2H), 7.15 (m, 2H), 7.33 (m, 2H).

EXAMPLE 16

(3S)-3-2-Hydroxy-2,2-dithien-2-ylacetylamino)-1-(3-phenoxypropyl)-1-azoniabicyclo[2.2.2]octane bromide The title compound was synthesised according to methods c and d. The yield of the final step was 0.36 g, 70.6%.

m.p.: 172.8-173.9° C.

MS [M-Br]$^+$: 483.

$^1$H-NMR (DMSO-d$_6$): δ 1.78 (m,$_1$H), 1.85-2.25 (m, 6H), 3.25-3.65 (m, 7H), 3.70-3.82 (m, 1H), 4.04 (t, 2H), 4.24 (m, 1H), 6.90-7.0 (m, 5H), 7.06 (m, 1H), 7.12 (m, 1H), 7.31 (m, 2H), 7.45 (m, 2H), 7.65 (s, 1H, OH), 8.74 (d, 1H, NH).

EXAMPLE 17

N-[(3R)-1-Azabicyclo[2.2.2]oct-3-yl]-2,2-dithien-2-ylacetamide

The title compound was synthesised according to method b. The yield was 0.31 g, 17.3%.

m.p.: 165° C.

MS [M+1]$^+$: 333. $^1$H-NMR (CDCl$_3$): δ 1.43 (m, 2H), 1.63 (m, 2H), 1.92 (m, 1H), 2.4 (m, 1H), 2.65-2.85 (m, 4H), 3.31 (m, 1H), 3.97 (m, 1H), 5.37 (s, 1H), 5.98 (d, 1H, NH), 7.0 (m, 4H), 7.28 (m, 2H).

EXAMPLE 18

(3R)-3-(2,2-Dithien-2-ylacetylamino)-1-(3-phenoxypropyl)-1-azoniabicyclo[2.2.2]octane bromide The title compound was synthesised according to methods b and d. The yield of the final step was 0.21 g, 79.8%.

m.p.: 135.6-137.1° C.

MS [M-Br]$^+$: 467.

$^1$H-NMR (DMSO-d$_6$): δ 1.83 (m, 1H), 1.94 (m, 2H), 2.0-2.25 (m, 4H), 3.19 (m, 1H), 3.30-3.55 (m, 6H), 3.86 (m, 1H), 4.03 (t, 2H), 4.18 (m, 1H), 5.65 (s, 1H), 6.93-6.98 (m, 5H), 7.01-7.06 (m, 2H), 7.31 (m, 2H), 7.42 (m, 2H), 9.10 (d, 1H, NH).

EXAMPLE 19

N-[(3R)-1-Azabicyclo[2.2.2]oct-3-yl]-2-cyclopentyl-2-hydroxy-2-thien-2-ylacetamide The title compound was synthesised as a mixture of diastereomers according to method b. The yield was 0.12 g, 27.9%.

MS [M+1]$^+$: 335.

$^1$H-NMR (DMSO-d$_6$): (mixture of diastereomers 50:50) δ 1.20-1.80 (m, 13H), 2.50-2.90 (m, 6H), 3.04 (m,1H), 3.69 (m, 1H), 5.98 & 6.01 (s, 1H, OH), 6.93 (m, 1 H), 7.08 (m, 1H), 7.35 (m, 1H), 7.59 (m, 1H, NH).

EXAMPLE 20

N-[(3R)-1-Azabicyclo[2.2.2]oct-3-yl]-2-hydroxy-2-thien-2-ylpent4-enamide

The title compound was synthesised as a mixture of diastereomers according to method c. The yield was 1.92 g, 82.4%.

m.p.: 54.4-58.3° C.

MS [M+1]$^+$: 307.

¹H-NMR (DMSO-d₆): (mixture of diastereomers) δ 1.25 (m, 1H), 1.40-1.75 (m, 4H), 2.45-2.70 (m, 5H), 2.70-3.10 (m, 3H), 3.65 (m, 1H), 5.0-5.10 (m, 2H), 5.60-5.80 (m, 1H), 6.50 & 6.52 (s, 1H, OH), 6.95 (m, 1H), 7.05 (m, 1H), 7.38 (m, 1H), 7.60 (d, 1H, NH).

EXAMPLE 21

(2*)-N-[(3R)-1-Azabicyclo[2.2.2]oct-3-yl]-2-hydroxy-2-thien-2-ylbutanamide (diastereomer 1, 70:30)

The title compound was synthesised according to method c. The yield was 0.19 g, 34% (based on single isomer).
m.p.: 139.0-140.7° C.
MS [M+1]⁺: 295.
¹H-NMR (DMSO-d6): (diastereomer 1, 70:30) δ 0.80 (t, 3H), 1.27 (m, 1H), 1.40-1.80 (m, 4H), 1.83 (m, 1H), 2.16 (m, 1H), 2.45-2.70 (m, 4H), 2.79 (m, 1H), 2.90-3.10 (m, 1H), 3.67 (m, 1H), 6.28 & 6.31 (s, 1H, OH), 6.94 (m, 1H), 7.03 (m, 1H), 7.36 (m, 1H), 7.62 (d, 1H, NH).
(*): Configuration not assigned.

EXAMPLE 22

(2*)-N-[(3R)-1-Azabicyclo[2.2.2]oct-3-yl]-2-hydroxy-2-thien-2-ylbutanamide (diastereomer 2, 27:73)

The title compound was synthesised according to method c. The yield was 0.42 g, 75% (based on single isomer).
m.p.: 68.9-70.2° C.
MS [M+1]⁺: 295.
¹H-NMR (DMSO-d₆): (diastereomer 2, 27:73) δ 0.82 (t, 3H), 1.26 (m, 1H), 1.40-1.80 (m, 4H), 1.86 (m, 1H), 2.17 (m, 1H), 2.45-2.70 (m, 4H), 2.78 (m, 1H), 2.90-3.10 (m, 1H), 3.67 (m,1H), 6.29 & 6.32 (s, 1H, OH), 6.93 (m, 1H), 7.03 (m, 1H), 7.36 (m,1H), 7.62 (d, 1H, NH).
(*): Configuration not assigned.

EXAMPLE 23

(2*)-N-[(3R)-1-Azabicyclo[2.2.2]oct-3-yl]-2-hydroxy-2-thien-2-ylbut-3-enamide (diastereomer 1)

The title compound was synthesised according to method c. The yield was 0.21 g, 18.9% (based on single isomer).
m.p.: 171.7-173.2° C.
MS [M+1]⁺: 293.
¹H-NMR (DMSO-d₆): (diastereomer 1) δ 1.27 (m, 1H), 1.40-1.75 (m, 4H), 2.50-2.70 (m, 4H), 2.77 (m, 1H), 3.0 (m, 1H), 3.66 (m. 1H), 5.18 (d,1H), 5.38 (d, 1H), 6.41 (dd, 1H), 6.71 (s, 1H, OH), 6.95 (m, 1H), 7.02 (m, 1H), 7.41 (m, 1H), 7.70 (d, 1H, NH).
(*): Configuration not assigned.

EXAMPLE 24

(2*)-N-[(3R)-1-Azabicyclo[2.2.2]oct-3-yl]-2-hydroxy-2-thien-2-ylbut-3-enamide (diastereomer 2)

The title compound was synthesised according to method c. The yield was 0.21 g, 18.9% (based on single isomer)
m.p.: 53.8-55.0° C.
MS [M+1]⁺: 293.
¹H-NMR (DMSO-d₆): (diastereomer 2) δ 1.27 (m, 1H), 1.40-1.75 (m, 4H), 2.50-2.70 (m, 4H), 2.81 (m, 1H), 3.03 (m, 1H), 3.69 (m, 1H), 5.21 (d, 1H), 5.40 (d, 1H), 6.45 (dd, 1H), 6.74 (s, 1H, OH), 6.96 (m, 1H), 7.01 (m, 1H), 7.41 (m, 1H), 7.72 (d, 1H, NH).
(*): Configuration not assigned.

EXAMPLE 25

N-[(3R)-1-Azabicyclo[2.2.2]oct-3-yl]-2,3-diphenylpropanamide

The title compound was synthesised as a mixture of diastereomers according to method a. The yield was 1.21 g, 82.3%.
m.p.: 142° C.
MS [M+1]⁺: 335.
¹H-NMR (DMSO-d₆): (mixture of diastereomers) δ 0.95-1.30 (m, 2H), 1.35-1.50 (m, 2H), 1.52 (m, 1H), 2.14-2.27 (m, 1H), 2.50-2.65 (m, 4H), 2.81-2.96 (m, 2H), 3.24-3.32 (m, 1H), 3.56 (m, 1H), 3.78-3.89 (m, 1H), 7.10-7.45 (m, 10H), 8.13 (m, 1H, NH).

EXAMPLE 26

N-[(3R)-1-Azabicyclo[2.2.2]oct-3-yl]-2-cyclopentyl-2-hydroxy-2-phenylacetamide

The title compound was synthesised as a mixture of diastereomers according to method b. The yield was 0.25 g, 28.4%.
m.p.: 69.8-73.3° C.
MS [M+1]⁺: 329.
¹H-NMR (DMSO-de): (mixture of diastereomers) δ 1.25 (m, 3H), 1.35-1.75 (m, 10H), 2.40-2.70 (m, 4H), 2.76 (m, 1H), 2.90-3.10 (m, 2H), 3.62 (m, 1H), 5.60 & 5.62 (s, 1H, OH), 7.20-7.23 (m, 1H), 7.27-7.33 (m, 2H), 7.52-7.61 (m, 3H).

EXAMPLE 27

N-[(3R)-1-Azabicyclo[2.2.2]oct-3-yl]-2-phenylhexanamide

The title compound was synthesised as a mixture of diastereomers according to method a. The yield was 1.59 g, 63.1%.
m.p.: 136° C.
MS [M+1]⁺: 301.
¹H-NMR (DMSO-d,): (mixture of diastereomers 50:50) δ 0.84 (t, 3H), 1.10-1.60 (m, 9H), 1.70 (m, 1H), 1.90 (m, 1H), 2.25-2.50 (m, 1H), 2.50-2.80 (m, 4H), 2.94 & 3.05 (m, 1H), 3.50 (m, 1H), 3.65 (m, 1H), 7.15-7.40 (m, 5H), 8.04 (m, 1H, NH).

EXAMPLE 28

N-(1-Azabicyclo[2.2.2]oct-3-yl)-9H-xanthene-9-carboxamide

The title compound was synthesised according to method b. The yield was 0.28 g, 19%.
m.p.: 251° C.
MS [M+1]⁺: 335.
¹H-NMR (DMSO-d₆): δ 1.25-1.60 (m, 3H), 1.67 (m, 1H), 1.82 (m, 1H), 2.40-2.50 (m, 1H), 2.55-2.75 (m, 3H), 2.82 (m, 1H), 3.06 (m, 1H), 3.62 (m, 1H), 5.0 (s, 1H), 7.05-7.15 (m, 4H), 7.25-7.35 (m, 4H), 8.51 (d, 1H, NH).

The title compound was also synthesised according to method a. The yield was 2.11 g, 52.6%.

EXAMPLE 29

1-Methyl-3-[(9H-xanthen-9-ylcarbonyl)amino]-1-azoniabicyclo[2.2.2]octane bromide The title compound was synthesised according to methods a and d. The yield of the final step was 0.25 g, 77.6%.
m.p.: 318° C.
MS [M-Br]$^+$: 349.
$^1$H-NMR (DMSO-d$_6$): δ 1.80-2.0 (m, 3H), 2.10 (m, 1H), 2.22 (m, 1H), 2.95 (s, 3H), 3.10-3.20 (m, 1H), 3.30-3.50 (m, 4H), 3.80 (m, 1H), 4.05 (m, 1H), 5.06 (s, 1H), 7.08-7.16 (m, 4H), 7.28-7.35 (m, 4H), 8.98 (d, 1H, NH).

EXAMPLE 30

1-(3-Phenoxypropyl)-3-[(9H-xanthen-9-ylcarbonyl)amino]-1-azoniabicyclo[2.2.2]octane bromide The title compound was synthesised according to methods a and d. The yield of the final step was 0.44 g, 100%.
m.p.: 242° C.
MS [M-Br]$^+$: 469.
$^1$H-NMR (DMSO-d$_6$): δ 1.80-2.0 (m, 3H), 2.05-2.30 (m, 4H), 3.25-3.70 (m, 7H), 3.82 (m, 1H), 4.05 (t, 2H), 4.10 (m, 1H), 5.15 (s, 1H), 6.90-7.0 (m, 3H), 7.05-7.20 (m, 4H), 7.25-7.42 (m, 6H), 9.16 (d, 1H, NH).

EXAMPLE 31

N-[(3R)-1-Azabicyclo[2.2.2]oct-3-yl]-9H-xanthene-9-carboxamide

The title compound was synthesised according to method a. The yield was 1.03 g, 43.4%.
m.p.: 239.7-241.4° C.
MS [M+1]$^+$: 335.
$^1$H-NMR (DMSO-d$_6$): δ 1.25-1.60 (m, 3H), 1.66 (m, 1H), 1.82 (m, 1H), 2.42-2.50 (m, 1H), 2.55-2.75 (m, 3H), 2.85 (m, 1H), 3.05 (m, 1H), 3.60 (m, 1H), 5.0 (s, 1H), 7.05-7.15 (m, 4H), 7.25-7.35 (m, 4H), 8.52 (d, 1H, NH).

EXAMPLE 32

(3R)-1-(3-Phenoxypropyl)-3-[(9H-xanthen-9-ylcarbonyl)amino]-1-azoniabicyclo[2.2.2]octane bromide The title compound was synthesised according to methods a and d. The yield of the final step was 0.48 g, 98%.
m.p.: 278.5-279.2° C.
MS [M-Br]$^+$: 469.
$^1$H-NMR (DMSO-d$_6$): δ 1.80-2.0 (m, 3H), 2.05-2.30 (m, 4H), 3.15-3.25 (m, 1H), 3.30-3.65 (m, 6H), 3.82 (m, 1H), 4.05 (t, 2H), 4.10 (m, 1H), 5.05 (s, 1H), 6.90-7.0 (m, 3H), 7.05-7.20 (m, 4H), 7.25-7.42 (m, 6H), 9.01 (d, 1H, NH).

EXAMPLE 33

N-[(3S)-1-Azabicyclo[2.2.2]oct-3-yl]-9H-xanthene-9-carboxamide

The title compound was synthesised according to method a. The yield was 1.1 g, 60%.
m.p.: 244.2-244.9° C.
MS [M+1]$^+$: 335.

$^1$H-NMR (DMSO-d$_6$): δ 1.25-1.60 (m, 3H), 1.66 (m, 1H), 1.82 (m, 1H), 2.42-2.50 (m, 1H), 2.55-2.75 (m, 3H), 2.83 (m, 1H), 3.05 (m, 1H), 3.60 (m, 1H), 5.0 (s, 1H), 7.05-7.15 (m, 4H), 7.25-7.35 (m, 4H), 8.53 (d, 1H, NH).

EXAMPLE 34

(3S)-1-Allyl-3-[(9H-xanthen-9-ylcarbonyl)amino]-1-azoniabicyclo[2.2.2]octane trifluoroacetate The title compound was synthesised according to methods a and e. The yield of the final step was 0.0091 g, 22.1%.
MS [M-CF$_3$COO]$^+$: 375.

EXAMPLE 35

(3S)-1-Heptyl-3-[(9H-xanthen-9-ylcarbonyl)amino]-1-azoniabicyclo[2.2.2]octane trifluoroacetate The title compound was synthesised according to methods a and e. The yield of the final step was 0.0097 g. 21.0%.
MS [M-CF$_3$COO]$^+$: 433.

EXAMPLE 36

(3S)-1-Cyclohexylmethyl-3-[(9H-xanthen-9-ylcarbonyl)amino]-1-azoniabicyclo[2.2.2]octane trifluoroacetate The title compound was synthesised according to methods a and e. The yield of the final step was 0.0124 g, 27.0%.
MS [M-CF$_3$COO]$^+$: 431.

EXAMPLE 37

(3S)-1-(3-Cyclohexylpropyl)-3-[(9H-xanthen-9-ylcarbonyl)amino]-1-azoniabicyclo[2.2.2]octane trifluoroacetate The title compound was synthesised according to methods a and e. The yield of the final step was 0.0045 g, 9.3%.
MS [M-CF$_3$COO]$^+$: 459.

EXAMPLE 38

(3S)-1-(3-Phenoxypropyl)-3-[(9H-xanthen-9-ylcarbonyl)amino]-1-azoniabicyclo[2.2.2]octane bromide The title compound was synthesised according to methods a and d. The yield of the final step was 0.28 g, 85%.
m.p.: 279.0-280.4° C.
MS [M-Br]$^+$: 469.
$^1$H-NMR (DMSO-d$_6$): δ 1.80-2.0 (m, 3H), 2.05-2.30 (m, 4H), 3.20-3.30 (m, 1H), 3.30-3.65 (m, 6H), 3.82 (m, 1H), 4.05 (t, 2H), 4.11 (m, 1H), 5.10 (s, 1H), 6.90-7.0 (m, 3H), 7.05-7.20 (m, 4H), 7.25-7.42 (m, 6H), 9.10 (d, 1H, NH).

EXAMPLE 39

(3S)-1-[3-(5,6,7,8-Tetrahydronaphthalen-2-yloxy)propyl]-3-[(9H-xanthen-9-ylcarbonyl)amino]-1-azoniabicyclo[2.2.2]octane trifluoroacetate The title compound was synthesised according to methods a and e. The yield of the final step was 0.0114 g, 21.2%.
MS [M-CF$_3$COO]$^+$: 523.

EXAMPLE 40

(3S)-1-[5-2,6-Dimethylphenoxy)pentyl]-3-[(9H-xanthen-9-ylcarbonyl)amino]-1-azoniabicyclo[2.2.2]octane trifluoroacetate The title compound was synthesised according to methods a and e. The yield of the final step was 0.0101 g, 18.7%.
MS [M-CF$_3$COO]$^+$: 525.

EXAMPLE 41

N-(1-Azabicyclo[2.2.2]oct-3-yl)-9-hydroxy-9H-fluorene-9-carboxamide

The title compound was synthesised according to method b. The yield was 1.06 g, 17.6%.
m.p.: 230° C.
MS [M+1]$^+$: 335.
$^1$H-NMR (CDCl$_3$): δ 1.0-1.30 (m, 2H), 1.52 (m, 2H), 1.79 (m, 1H), 2.04 (m, 1H), 2.36 (m, 1H), 2.57 (m, 3H), 3.05 (m, 1H), 3.77 (m, 1H), 5.45 (bs, 1H), 5.71 (d, 1H, NH), 7.20-7.50 (m, 6H), 7.55-7.70 (m, 2H).

EXAMPLE 42

3-{[(9-Hydroxy-9H-fluoren-9-yl)carbonyl]amino}-1-methyl-1-azoniabicyclo[2.2.2]octane bromide The title compound was synthesised according to methods b and d. The yield of the final step was 0.26 g, 83.8%.
m.p.: 197.5-203.6° C.
MS [M-Br]$^+$: 349.
$^1$H-NMR (DMSO-d$_6$): δ 1.80-2.0 (m, 3H), 2.10-2.25 (m, 2H), 2.96 (s, 3H), 3.35-3.70 (m, 5H), 3.78 (m, 1H), 4.15 (m, 1H), 6.82 (s, 1H, OH), 7.30 (m, 2H), 7.43 (m, 4H), 7.79 (m, 2H), 8.81 (d, 1H, NH).

EXAMPLE 43

3-{[(9-Hydroxy-9H-fluoren-9-yl)carbonyl]amino}-1-(3-phenoxypropyl)-1-azoniabicyclo[2.2.2]octane bromide The title compound was synthesised according to methods b and d. The yield of the final step was 0.35 g, 87.5%.
m.p.: 264° C.
MS [M-Br]$^+$: 469.
$^1$H-NMR (DMSO-d$_6$): δ 1.80-2.0 (m, 3H), 2.10-2.30 (m, 4H), 3.30-3.55 (m, 5H), 3.67 (m, 2H), 3.79 (m, 1H), 4.08 (t, 2H), 4.20 (m, 1H), 6.82 (s, 1H, OH), 6.97 (m, 3H), 7.32 (m, 4H), 7.43 (m, 4H), 7.79 (m, 2H), 8.88 (d, 1H, NH).

EXAMPLE 44

N-[(3R)-1-Azabicyclo[2.2.2]oct-3-yl]-9-hydroxy-9H-fluorene-9-carboxamide

The title compound was synthesized according to method b. The yield was 0.304 g, 4%.
MS [M+1]$^+$: 335
$^1$H-RMN (CDCl$_3$): δ 7.67-7.62 (m, 2H), 7.42-7.36 (m, 4H), 7.32-7.25 (m, 2H), 6.08-5.93 (m, NH, 1H), 3.74 (m, 1H), 3.00-2.87 (m, 1H), 2.52-2.27 (m, 4H), 2.02-1.92 (m, 1H) 1.80-1.76 (m, 1H), 1.51-1.44 (m, 2H), 1.26-1.17 (m, 2H).

EXAMPLE 45

N-[(3R)-1-Azabicyclo[2.2.2]oct-3-yl]-2-fur-2-yl-2-hydroxypent-3-ynamide

The title compound was synthesized as a mixture of diastereomers according to method c. The yield was 1.38 g, 39%
MS [M+1]$^+$: 289
$^1$H-RMN (CDCl$_3$): (mixture of diastereomers) δ 7.36-7.35 (m, 1H), 6.87-6.76 (m, NH, 1H), 6.54-6.52 (m, 1H), 6.34-6.32 (m, 1H), 3.92 (m, 1H), 3.29-3.17 (m, 1H), 2.78-2.64 (m, 4H), 2.47-2.35 (m, 1H), 2.00-1.90 (m, 1H), 1.92 (s, 3H), 1.70-1.39 (m, 4H).

EXAMPLE 46

N-[(3R)-1-Azabicyclo[2.2.2]oct-3-yl]-2-fur-2-yl-2-hydroxy4-(4-methoxyphenyl)butanamide The title compound was prepared as a mixture of diastereomers according to method c. The yield was 2.4 g, 44%
MS [M+1]$^+$: 385
$^1$H-RMN (CDCl$_3$): (mixture of diastereomers) δ 7.39-7.38 (m, 1H), 7.09 (d, 2H), 6.82 (d, 2H), 6.70-6.67 (m, NH, 1H), 6.41-6.35 (m, 2H), 3.92 (m, 1H), 3.78 (s, 3H), 3.33-3.24 (m, 1H), 2.82-2.19 (m, 9H), 1.96-1.87 (m, 1H), 1.67-1.40 (m, 4H)

EXAMPLE 47

N-[(3R)-1-Azabicyclo[2.2.2]oct-3-yl]-N-methyl-9H-xanthene-9-carboxamide

The title product was synthesized according to method a. The yield was 0.9 g, 50%.
MS [M+1]$^+$: 349
$^1$H-RMN (400 MHz, 60° C., CDCl$_3$): δ 7.26-7.19 (m, 4H), 7.10-7.01 (m, 4H), 5.51 (s, 1H), 4.18 (broad multiplet, 1H), 2.92 (s, 3H), 2.85-2.40 (m, 6H), 1.85-1.20 (m, 5H)

EXAMPLE 48

N-[(3R)-1-Azabicyclo[2.2.2]oct-3-yl]-2-5-bromothien-2-yl)-2-(4-fluoro-3-methylphenyl)-2-hydroxyacetamide The title compound was synthesized as a mixture of diastereomers according to method c. The yield was 2.1 g, 42%.
MS [M+1]$^+$: 453. 455
$^1$H-RMN (CDCl$_3$): (mixture of diastereomers) δ 7.35-7.20 (m, 2H), 7.08-6.89 (m, 3H), 6.80 (dd, 1H), 3.93-3.84 (m, 1H), 3.18-3.07 (m, 1H), 2.69-2.58 (m, 4H), 2.33-2.22 (m, 4H), 1.92-1.87 (m, 1H), 1.63-1.42 (m, 4H)

EXAMPLE 49

(2S)-N-[(3R)-1-azabicyclo[2.2.2]oct-3-yl]-2-cyclopentyl-2-hydroxy-2-thien-2-ylacetamide The title compound was synthesized according to method b. The yield was 0.650 g, 44%.
MS [M+1]$^+$: 335 $^1$H-RMN (CDCl$_3$): δ 7.24 (m, 1H), 7.08 (m, 1H), 6.97 (m, 1H), 6.64 (d, NH, 1H), 3.91-3.81 (m, 1H), 3.33-3.23 (m, 1H), 2.88-2.69 (m, 5H), 2.42-2.33 (m, 1H), 1.87 (m, 1H), 1.69-1.36 (m, 12H)

EXAMPLE 50

(3R)-1-[3-(Benzothiazol-2-yloxy)propyl]-3-(2-fur-2-yl-2-hydroxypent-3-ynoylamino)-1-azonia-bicyclo[2.2.2]octane chloride The title compound was synthesized as a mixture of diastereomers according to methods c and d.

The reaction time for the final step (conditions:THF, reflux temperature) was 7 days. The obtained product was purified by several washings with ether. The yield was 0.337 g (75%).

MS [M-Cl]$^+$: 480

HPLC: mixture of diastereomers 49:51

$^1$H-NMR (DMSO-d$_6$): (mixture of diastereomers) δ 8.53-8.49 (m, NH, 1H), 7.69 (m, 1H), 7.58 (m, 1H), 7.53-7.39 (m, 2H), 7.26-7.19 (m, 2H), 6.43-6.38 (m, 2H), 4.20-4.14 (m, 1H), 4.05-3.99 (m, 2H), 3.76-3.65 (m, 1H), 3.60-3.20 (m, 7H), 2.20-1.87 (s,3H)

EXAMPLE 51

(3R)-3-(2-Fur-2-yl-2-hydroxypent-3-ynoylamino)-1-[3-(naphthalen-1-yloxy)propyl]-1-azoniabicyclo[2.2.2]octane chloride The title compound was synthesized as a mixture of diastereomers according to methods c and d.

The reaction time for the final step (conditions, THF, reflux temperature) was 7 days. The obtained product was purified by several washings with ether. The yield was 0.252 g (57%).

MS [M-Cl]$^+$: 473

HPLC: mixture of diastereomers 48:52 $^1$H-NMR (DMSO-d$_6$): (mixture of diastereomers) δ 8.62-8.58 (m, NH, 1H), 8.23 (m, 1H), 7.90-7.86 (m, 1H), 7.61-7.40 (m, 5H), 7.25 (m, 1H), 6.99 (m, 1H), 6.46-6.39 (m, 2H), 4.30-4.20 (m, 3H), 3.95-3.30 (m, 8H), 2.42-2.25 (m, 2H), 2.20-1.70 (m, 5H), 1.89 (s, 3H).

EXAMPLE 52

(3R)-1-[3-Benzo[1,3]dioxol-5-yloxy)propyl]-3-(2-fur-2-yl-2-hydroxypent -3-ynoylamino)-1-azonia-bicyclo[2.2.2]octane bromide The title compound was synthesised as a mixture of diastereomers according to methods c and d.

The reaction time for the final step (conditions, THF, reflux temperature) was 2 days. The obtained product was purified by several washings with ether. The yield was 0.320 g (78%).

MS [M-Br]$^+$: 467

HPLC: mixture of diastereomers 52:48

$^1$H-NMR (DMSO-d$_6$): (mixture of diastereomers) δ 8.54-8.49 (m, NH, 1H), 7.60 (s, 1H), 7.21 (d, 1H), 6.82 (d, 1H), 6.65 (m, 1H), 6.45-6.36 (m, 3H), 5.96 (s, 2H), 4.26-4.15 (m, 1H), 4.00-3.95 (m, 2H), 3.82-3.70 (m, 1H), 3.61-3.28 (m, 7H), 2.15-1.74 (m, 7H), 1.89 (s, 3H).

EXAMPLE 53

(3R)-3-{[(2S)-2-Cyclopentyl-2-hydroxy-2-thien-2-ylacetyl]amino}-1-(4,4,4-trifluorobutyl)-1-azoniabicyclo[2.2.2]octane bromide The title compound was synthesised according to method d from Example 49. The reaction time (conditions, THF, reflux temperature) was 3 days. The obtained product was purified by several washings with ether. The yield was 0.183 g (77%).

MS [M-Br]$^+$: 445

$^1$H-NMR (DMSO-d$_6$): δ 8.28 (d, NH, 1H), 7.38 (dd, 1H), 7.09 (dd, 1H), 6.94 (dd, 1H), 6.11 (s, OH, 1H), 4.21-4.12 (m,1H), 3.72 (m, 1H), 3.59-3.30 (m, 5H), 3.25-3.17 (m, 2H), 2.80 (m, 1H), 2.41-2.25 (m, 2H), 2.05-1.80 (m, 6H), 1.80-1.62 (m, 1H), 1.62-1.30 (m, 8H)

EXAMPLE 54

(3R)-3-{[(2S)-2-Cyclopentyl-2-hydroxy-2-thien-2-ylacetyl]amino}-1-(2-hydroxyethyl)-1-azoniabicyclo[2.2.2]octane bromide The title compound was synthesised according to method d from Example 49. The reaction time (conditions: THF, reflux temperature) was 5 days. The obtained product was purified by several washings with ether. The yield was 0.174 g (84%).

MS [M-Br]$^+$: 379

$^1$H-NMR (DMSO-d$_6$): δ 8.24 (d, NH, 1H), 7.37 (dd,1H), 7.08 (dd, 1H), 6.94 (dd, 1H), 6.10 (s, OH, 1H), 5.27 (t, OH, 1H), 5.20-5.10 (m, 1H), 4.15 (m, 1H), 3.85-3.75 (m, 2H), 3.75-3.20 (m, 5H), 2.83-2.77 (m,1H), 2.00-1.85 (m, 4H), 1.77-1.66 (m, 1H), 1.53-1.41 (m, 8H)

EXAMPLE 55

(3R)-1-(4-Acetoxybutyl)-3-[2-(5-bromothien-2-yl)-2-(4-fluoro-3-methylphenyl)-2-hydroxyacetylamino]-1-azoniabicyclo[2.2.2]octane bromide The title compound was synthesised as a mixture of diastereomers according to methods c and d. The reaction time for the final step (conditions: THF, reflux temperature) was 41 hours. The obtained product was purified by several washings with ether. The yield was 0.190 g (88%).

MS [M-Br]$^+$: 569, 567

$^1$H-NMR (DMSO-d$_6$): (mixture of diastereomers) δ 8.72 (d, NH, 1H), 7.45 (d,1H), 7.36-7.18 (m, 2H), 7.13-7.06 (m, 2H), 6.91 (t, 1H), 4.25-4.18 (m, 1H), 4.06-4.00 (m, 2H), 3.72-3.26 (m, 6H), 3.19-3.11 (m, 2H), 2.20 (s, 3H), 2.21-1.84 (m,$_1$H), 2.02 (s, 3H), 1.95-1.54 (m, 8H)

EXAMPLE 56

(3R)-3-[2-(5-Bromothien-2-yl)-2-(4-fluoro-3-methylphenyl)-2-hydroxyacetylamino]-1-(4-ethoxycarbonylbutyl)-1-azoniabicyclo[2.2.2]octane bromide The title compound was synthesised as a mixture of diastereomers according to methods c and d. The reaction time for the final step (conditions: THF, reflux temperature) was 46 hours. The obtained product was purified by several washings with ether. The yield was 0.201 g (92%).

MS [M-Br]$^+$: 583, 581

$^1$H-NMR (DMSO-d$_6$): (mixture of diastereomers) δ 8.72 (d, NH, 1H), 7.45 (d, 1H), 7.36-7.18 (m, 2H), 7.13-7.06 (m, 2H), 6.91 (t$_1$ H), 4.26-4.16 (m, 1H), 4.06 (q, 2H), 3.65-3.30 (m, 6H), 3.18-3.09 (m, 2H), 2.40-2.32 (m, 2H), 2.20 (s, 3H), 2.08-1.48 (m, 9H), 1.18 (t, 3H)

EXAMPLE 57

(3R)-1-(3-Cyanopropyl)-3-[2-fur-2-yl-2-hydroxy-4-(4-methoxyphenyl)butyrylamino]-1-azoniabicyclo[2.2.2]octane bromide The title compound was synthesised as a mixture of diastereomers according to methods c and d. The reaction time for the final step (conditions: THF, reflux temperature) was 3 days. The obtained product was purified by several washings with ether. The yield was 0.113 g (65%).

MS [M-Br]$^+$: 452

$^1$H-NMR (DMSO-d$_6$): (mixture of diastereomers) δ 8.49-8.40 (m, NH, 1H), 7.58 (s, 1H), 7.09 (d, 2H), 6.84 (d, 2H), 6.41-6.35 (m, 2H), 6.33 (d, 1H), 4.27-4.19 (m, 1H), 3.80-3.65 (m, 1H), 3.71 (s, 3H), 3.63-3.36 (m, 5H), 3.23-3.17 (m, 2H), 2.68-2.60 (m, 3H), 2.40-1.73 (m, 10H)

EXAMPLE 58

(3R)-1-(2-[1,3]Dioxolan-2-yl-ethyl)-3-[2-fur-2-yl-2-hydroxy-4-(4-methoxy phenyl)butyrylamino]-1-azoniabicyclo[2.2.2]octane bromide The title compound was synthesised as a mixture of diastereomers according to methods c and d. The reaction time for the final step (conditions: THF, reflux temperature) was 3 days. The obtained product was purified by several washings with ether. The yield was 0.128 9 (70%).

MS [M-Br]$^+$: 485

$^1$H-NMR (DMSO-d$_6$): (mixture of diastereomers) δ 8.47-8.37 (m, NH, 1H), 7.58 (s, 1H), 7.09 (d, 2H), 6.84 (d, 2H), 6.40-6.35 (m, 2H), 6.32 (d, 1H), 4.94-4.90 (m, 1H), 4.21 (m, 1H), 3.96-3.77 (m, 4H), 3.71 (s, 3H), 3.59-3.21-(m, 7H), 2.72-2.61 (m, 1H), 2.41-1.74 (m, 10H).

EXAMPLE 59

(3R)-3-{[(9-Hydroxy-9H-fluoren-9-yl)carbonyl]amino}-1-[3-(methylphenylamino)propyl]-1-azoniabicyclo[2.2.2]octane chloride The title compound was synthesised according to methods b and d. The reaction time for the final step (conditions: THF:CHCl$_3$ 1:1, reflux temperature) was 20 days. The obtained product was purified by washing with hot CHCl$_3$ and ether. The yield was 0.052 g (33%).

MS [M-Cl]$^+$: 482

$^1$H-NMR (DMSO-d$_6$): δ 8.86 (d, NH, 1H), 7.78 (d, 2H), 7.45-7.16 (m, 8H), 6.81-6.62 (m, 4H), 4.23-4.14 (m, 1H), 3.76-3.53 (m, 2H), 3.43-3.17 (m, 8H), 2.91 (s, 3H), 2.23-1.77 (m, 7H).

EXAMPLE 60

(3R)-3-[Methyl-(9H-xanthen-9-ylcarbonyl)amino]-1-(3-pyrrol-1-ylpropyl)-1-azoniabicyclo[2.2.2]octane bromide The title compound was synthesised according to methods a and d. The reaction time for the final step (conditions: THF, reflux temperature) was 2 days. The obtained product was purified by several washings with THF and ether. The yield was 0.257 g (83%).

MS [M-Br]$^+$: 456

H-NMR (DMSO-d$_6$): δ 7.34-7.06 (m, 8H), 6.78 (m, 2H), 6.01 (m, 2H), 5.75 (s, 1H), 4.47 (m, 1H), 3.94-3.88 (m, 2H), 3.72-3.25 (m, 6H), 3.39 (s, 3H), 3.20-3.05 (m, 2H), 2.22-1.88 (m, 7H).

EXAMPLE 61

(3R)-1-[3-(Biphenyl4-yloxy)propyl]-3-[methyl-(9H-xanthene-9-carbonyl)amino]-1-azoniabicyclo[2.2.2]octane chloride The title compound was synthesised according to methods a and d. The reaction time for the final step (conditions: THF, reflux temperature) was 11 days. The obtained product was purified by several washings with THF and ether. The yield was 0.195 g (57%).

MS [M-Cl]$^+$: 559

$^1$H-NMR (DMSO-d$_6$): δ 7.62 (d, 4H), 7.47-7.02 (m, 13H), 5.77 (s, 1H), 4.50 (m, 1H), 4.13-4.06 (m, 2H), 3.82-3.31 (m, 8H), 3.42 (s, 3H), 2.25-1.91 (m, 7H).

The following examples illustrate pharmaceutical compositions according to the present invention and procedures for their preparation.

EXAMPLE 62

Preparation of a Pharmaceutical Composition: Tablets

| Formulation: | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

EXAMPLE 63

Preparation of a Pharmaceutical Composition: Coated Tablets

| Formulation: | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |

-continued

| Formulation: | |
|---|---|
| Hydroxypropylcellulose | 2.3 mg |
| Polyethylene glycol 6000 | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight.

Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 64

Preparation of a Pharmaceutical Composition: Liquid Inhalant

| Formulation: | |
|---|---|
| Compound of the present invention | 400 μg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° C. for 30 minutes to give a liquid inhalant.

EXAMPLE 65

Preparation of a Pharmaceutical Composition: Powder Inhalant

| Formulation: | |
|---|---|
| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 66

Preparation of a Pharmaceutical Composition: Inhalation Aerosol

| Formulation: | |
|---|---|
| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapour (purging ingredients should not contain more than 1 ppm oxygen) and is sealed with valve. 11.2344 g of HFC-134A propellant is then pressure filled into the sealed container.

The invention claimed is:

1. A compound of formula (II)

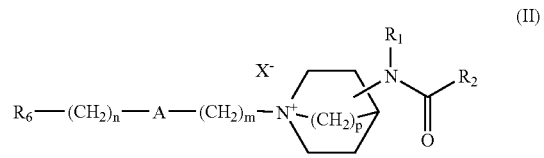

wherein
$R_1$ represents a hydrogen atom or a straight or branched, optionally substituted lower alkyl group;
$R_2$ represents a group of formula i) or ii)

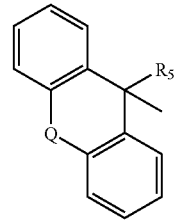

wherein:
$R_3$ represents a group chosen from phenyl, 2-furyl, 3-furyl, 2-thienyl and 3-thienyl;
$R_4$ represents a group chosen from optionally substituted lower alkyl, optionally substituted lower alkenyl, optionally substituted lower alkynyl, cycloalkyl, cycloalkylmethyl, phenyl, benzyl, phenethyl, 2-furyl, 3-furyl, 2-thienyl and 3-thienyl; and
$R_5$ represents a hydrogen atom or a hydroxy, methyl, or —$CH_2OH$ group;

wherein the benzene rings in formula ii) and the cyclic groups represented by $R_3$ and $R_4$ are each independently optionally substituted by one, two or three, identical or different, substituents chosen from halogen, straight or branched, optionally substituted lower alkyl, hydroxy, straight or branched, optionally substituted lower alkoxy, nitro, cyano, —$CO_2R'$ and —NR'R", wherein R' and R" each independently represents a hydrogen atom or a straight or branched, optionally substituted lower alkyl group or R' and R" together with the atom to which they are attached form a cyclic group;

Q represents a single bond or a —$CH_2$—, —$CH_2$—$CH_2$—, —O—, —O—$CH_2$—, —S—, —S—$CH_2$— or —CH=CH— group; and p is 1 or 2 and the amide group is at positions 2, 3 or 4 of the azabicyclic ring;

m is an integer ranging from 0 to 8;

n is an integer ranging from 0 to 4:

A represents a group chosen from —$CH_2$—, —CH=CR'—, —CR'=CH—, —CR'R"—, —C(O)—, —O—, —S—, —S(O)—, —$S(O)_2$— and —NR'—, wherein R' and R" each independently represents a hydrogen atom or a straight or branched, optionally substituted lower alkyl group or R' and R" together with the atom to which they are attached form a cyclic group;

$R_6$ represents a hydrogen atom, or a group chosen from straight or branched, optionally substituted lower alkyl, hydroxy, straight or branched, optionally substituted lower alkoxy, cyano, nitro, —CH=CR'R", —C(O)OR', —OC(O)R', —SC(O)R', —C(O)NR'R", —NR'C(O)OR", —NR'C(O)NR", cycloalkyl, phenyl, naphthanelyl, 5,6,7,8-tetrahydronaphthanelyl, benzo[1,3]dioxolyl, heteroaryl and heterocyclyl; wherein R' and R" each independently represents a hydrogen atom or a straight or branched, optionally substituted lower alkyl group or R' and R" together with the atom to which they are attached form a cyclic group;

and wherein the cyclic groups represented by $R_6$ are optionally substituted by one, two or three, identical or different, substituents chosen from halogen, hydroxy, straight or branched, optionally substituted lower alkyl, phenyl, —OR', —SR', —NR'R", —NHCOR', —CONR'R", —CN, —$NO_2$ and —COOR'; wherein R' and R" each independently represents a hydrogen atom or a straight or branched, optionally substituted lower alkyl group or R' and R" together with the atom to which they are attached form a cyclic group; and $X^-$ represents a pharmaceutically acceptable anion of a mono or polyvalent acid, or a stereoisomer or mixture thereof;

with the proviso that when p is 2, the amide moiety is in position 3 of the quinuclidine ring, $R_1$ is hydrogen, $R_3$ and $R_4$ are both unsubstituted phenyl and $R_5$ is hydroxy, then in the compounds of formula (II) the sequence $R_6$—$(CH_2)_n$-A-$(CH_2)_m$— cannot be a methyl group; and wherein when a methyl group is attached to the nitrogen atom of the quinuclidine ring, then $R_5$ cannot be hydroxy.

2. The compound according to claim 1, wherein, m is an integer ranging from 0 to 6;

n is an integer ranging from 0 to 4;

A represents a group chosen from —$CH_2$—, —CH=CH—, —O—, —C(O)—, —NR'—, and —S—; and $R_6$ is a hydrogen atom, a cyano group, a nitro group, a —C(O)OR' group, a —OC(O)R'group, a —SC(O)R' group, a —CH=$CH_2$ group, a —CH=CR'R" group, a C(O)NR'R" group, a straight or branched $C_1$-$C_4$ alkyl group, which is optionally substituted with at least one halogen atom, a straight $C_1$-$C_4$ alkoxy group, which is optionally substituted with at least one substituent chosen from halogen atoms, hydroxy groups, and a cyclic group, which is optionally substituted with at least one substituent chosen from halogen atoms, groups of formula —C(O)NR'R" and methyl, hydroxy, nitro and phenyl groups, wherein the cyclic group is chosen from cyclohexyl, phenyl, 5,6,7,8-tetrahydronaphthanelyl, 2-thienyl, 1-pyrrolidinyl, 1-pyrrolyl, benzo[1,3]dioxolyl, 2-benzothiazolyl, naphthalenyl and dioxolyl.

3. The compound according to claim 2, wherein, m is an integer ranging from 0 to 5;

n is an integer ranging from 0 to 2;

A represents a group chosen from —$CH_2$—, —CH=CH—, —O—, —C(O)—, —NR'—, and —S—; and $R_6$ is a hydrogen atom, a cyano group, a —C(O)OR'group, a —OC(O)R' group, a —SC(O)R' group, a —CH=$CH_2$ group, a —C(O)NR'R" group, a straight or branched $C_1$-$C_4$ alkyl group, a trifluoromethyl, or a cyclic group chosen from cyclohexyl, 5,6,7,8-tetrahydronaphthanelyl, 2-thienyl, 1-pyrrolyl, benzo[1,3]dioxolyl, 2-benzothiazolyl, naphthalenyl, dioxolyl and phenyl, wherein the cyclic group is optionally substituted with at least one substituent chosen from halogen atoms, groups of formula —C(O)NR'R", methyl, hydroxy and phenyl groups.

4. The compound according to claim 3, wherein, m is an integer ranging from 0 to 5;

n is an integer ranging from 0 to 2;

A represents a group chosen from —$CH_2$—, —CH=CH—, and —O—; and $R_6$ is chosen from hydrogen, straight $C_1$-$C_4$ alkyl group, —CH=$CH_2$ group, cyclohexyl group, and a phenyl group, wherein the phenyl group is optionally substituted with one or two, identical or different, substituents chosen from methyl groups and hydroxy groups, 5,6,7,8-tetrahydronaphthanelyl and 2-thienyl.

5. The compound according to claim 4, wherein the sequence $R_6$—$(CH_2)_n$-A-$(CH_2)_m$— is chosen from methyl, 3-phenoxypropyl, 3-(3-hydroxyphenoxy)propyl, allyl, heptyl, 3-phenylpropyl, 3-phenylallyl, 2-phenoxyethyl, 2-benzyloxyethyl, cyclohexylmethyl, 3-(5,6,7,8-tetrahydronaphthalen-2-yloxy)propyl, 5-(2,6-dimethylphenoxy)pentyl, 3-thien-2-ylpropyl and 3-cyclohexyipropyl and $X^-$ is bromide or trifluoroacetate.

6. A process for producing a compound of claim 1, wherein the process comprises reacting a compound of formula (I)

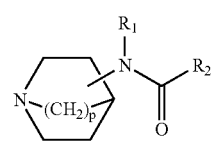

(I)

wherein:

$R_1$ represents a hydrogen atom or a straight or branched, optionally substituted lower alkyl group;

$R_2$ represents a group of formula i) or ii)

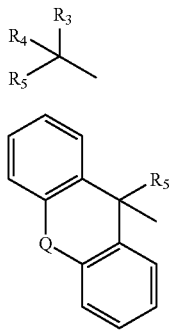

wherein:
- R₃ represents a group chosen from phenyl, 2-furyl, 3-furyl, 2-thienyl and 3-thienyl;
- R₄ represents a group chosen from optionally substituted lower alkyl, optionally substituted lower alkenyl, optionally substituted lower alkynyl, cycloalkyl, cycloalkylmethyl, phenyl, benzyl, phenethyl, 2-furyl, 3-furyl, 2-thienyl and 3-thienyl; and
- R₅ represents a hydrogen atom or a hydroxy, methyl, or —CH₂OH group; wherein the benzene rings in formula ii) and the cyclic groups represented by R₃ and R₄ are each independently optionally substituted by one, two or three, identical or different, substituents chosen from halogen, straight or branched, optionally substituted lower alkyl, hydroxy, straight or branched, optionally substituted lower alkoxy, nitro, cyano, —CO₂R' and —NR'R", wherein R' and R" each independently represents a hydrogen atom or a straight or branched, optionally substituted lower alkyl group or R' and R" together with the atom to which they are attached form a cyclic group;
- Q represents a single bond or a —CH₂—, —CH₂—CH₂—, —O—, —O—CH₂—, —S—, —S—CH₂— or —CH=CH— group; and
- p is 1 or 2 and the amide group is at positions 2, 3 or 4 of the azabicyclic ring; or pharmaceutically acceptable salt thereof, or a stereoisomer or a mixture thereof;

with the proviso that when p is 2, the amide moiety is in position 3 of the quinuclidine ring, R₁ is hydrogen and R₃ and R₄ are both unsubstituted phenyl, then
when the compound is not a pharmaceutically acceptable salt or is a HCl salt, then R₅ cannot be one of hydrogen or hydroxy; and
when the compound is a quaternary ammonium salt having a methyl group attached to the nitrogen atom of the quinuclidine ring, then R₅ cannot be hydroxy, with an alkylating agent of formula R₆—(CH₂)ₙ-A-(CH₂)ₘ-W, wherein
W represents a suitable leaving group.

7. The compound according to claim 1, chosen from:
3-(2-Hydroxy-2,2-dithien-2-ylacetylamino)-1-methyl-1-azoniabicyclo[2.2.2]octane bromide;
3-(2-Hydroxy-2,2-dithien-2-ylacetylamino)-1-(3-phenoxypropyl)-1-azoniabicyclo[2.2.2]octane bromide;
(3R)-3-(2-Hydroxy-2,2-dithien-2-ylacetylamino)-1-methyl-1-azoniabicyclo[2.2.2]octane trifluoroacetate;
(3R)-1-Allyl-3-(2-hydroxy-2,2-dithien-2-ylacetylamino)-1-azoniabicyclo[2.2.2]octane trifluoroacetate;
(3R)-1-Heptyl-3-(2-hydroxy-2,2-dithien-2-ylacetylamino)-1-azoniabicyclo[2.2.2]octane trifluoroacetate;
(3R)-3-(2-Hydroxy-2,2-dithien-2-ylacetylamino)-1-(3-phenylpropyl)-1-azoniabicyclo[2.2.2]octane bromide;
(3R)-3-(2-Hydroxy-2,2-dithien-2-ylacetylamino)-1-((E)-3-phenylallyl)-1-azoniabicyclo[2.2.2]octane trifluoroacetate;
(3R)-3-(2-Hydroxy-2,2-dithien-2-ylacetylamino)-1-(2-phenoxyethyl)-1-azoniabicyclo[2.2.2]octane bromide;
(3R)-3-(2-Hydroxy-2,2-dithien-2-ylacetylamino)-1-(3-phenoxypropyl)-1-azoniabicyclo[2.2.2]octane bromide;
(3R)-3-(2-Hydroxy-2,2-dithien-2-ylacetylamino)-1-[3-(3-hydroxyphenoxy)propyl]-1-azoniabicyclo[2.2.2]octane trifluoroacetate;
(3R)-1-(2-Benzyloxyethyl)-3-(2-hydroxy-2,2-dithien-2-ylacetylamino)-1-azoniabicyclo[2.2.2]octane trifluoroacetate;
(3R)-3-(2-Hydroxy-2,2-dithien-2-ylacetylamino)-1-(3-thien-2-ylpropyl)-1-azoniabicyclo[2.2.2]octane bromide;
(3S)-3-(2-Hydroxy-2,2-dithien-2-ylacetylamino)-1-(3-phenoxypropyl)-1-azoniabicyclo[2.2.2]octane bromide;
(3R)-3-(2,2-Dithien-2-ylacetylamino)-1-(3-phenoxypropyl)-1-azoniabicyclo[2.2.2]octane bromide;
1-Methyl-3-[(9H-xanthen-9-ylcarbonyl)amino]-1-azoniabicyclo[2.2.2]octane bromide;
1-(3-Phenoxypropyl)-3-[(9H-xanthen-9-ylcarbonyl)amino]-1-azoniabicyclo[2.2.2]octane bromide;
(3R)-1-(3-Phenoxypropyl)-3-[(9H-xanthen-9-ylcarbonyl)amino]-1-azoniabicyclo[2.2.2]octane bromide;
(3S)-1-Allyl-3-[(9H-xanthen-9-ylcarbonyl)amino]-1-azoniabicyclo[2.2.2]octane trifluoroacetate;
(3S)-1-Heptyl-3-[(9H-xanthen-9-ylcarbonyl)amino]-1-azoniabicyclo[2.2.2]octane trifluoroacetate;
(3S)-1-Cyclohexylmethyl-3-[(9H-xanthen-9-ylcarbonyl)amino]-1-azoniabicyclo[2.2.2]octane trifluoroacetate;
(3S)-1-(3-Cyclohexylpropyl)-3-[(9H-xanthen-9-ylcarbonyl)amino]-1-azoniabicyclo[2.2.2]octane trifluoroacetate;
(3S)-1-(3-Phenoxypropyl)-3-[(9H-xanthen-9-ylcarbonyl)amino]-1-azoniabicyclo[2.2.2]octane bromide;
(3S)-1-[3-(5,6,7,8-Tetrahydronaphthalen-2-yloxy)propyl]-3-[(9H-xanthen-9-ylcarbonyl)amino]-1-azoniabicyclo[2.2.2]octane trifluoroacetate;
(3S)-1-[5-(2,6-Dimethylphenoxy)pentyl]-3-[(9H-xanthen-9-ylcarbonyl)amino]-1-azoniabicyclo[2.2.2]octane trifluoroacetate;
3-{[(9-Hydroxy-9H-fluoren-9-yl)carbonyl]amino}-1-methyl-1-azoniabicyclo[2.2.2]octane bromide;
3-{[(9-Hydroxy-9H-fluoren-9-yl)carbonyl]amino}-1-(3-phenoxypropyl)-1azoniabicyclo[2.2.2]octane bromide;
(3R)-1-[3-(2-Carbamoylphenoxy)propyl]-3-{[(9-Hydroxy-9H-fluoren-9-yl)carbonyl]amino}-1-azoniabicyclo[2.2.2]octane formate;
(3R)-1-[4-(4-Fluorophenyl)-4-oxobutyl]-3-{[(9-Hydroxy-9H-fluoren-9-yl)carbonyl]amino}-1-azoniabicyclo[2.2.2]octane formate;
(3R)-3-{[(9-Hydroxy-9H-fluoren-9-yl)carbonyl]amino}-1-[3-(methylphenylamino)propyl]-1-azoniabicyclo[2.2.2]octane chloride;
(3R)-3-{[(9-Hydroxy-9H-fluoren-9-yl)carbonyl]amino}-1-(3-phenylsulfanylpropyl)-1-azoniabicyclo[2.2.2]octane formate;
(3R)-3-[Methyl-(9H-xanthen-9-ylcarbonyl)amino]-1-(3-pyrrol-1-ylpropyl)-1-azoniabicyclo[2.2.2]octane bromide;

(3R)-1-[3-(Biphenyl-4-yloxy)propyl]-3-[methyl-(9H-xanthene-9-carbonyl)amino]-1-azoniabicyclo[2.2.2]octane chloride;

(3R)-3-(2-Fur-2-yl-2-Hydroxypent-3-ynoylamino)-1-[3-(naphthalen-1-yloxy)propyl]-1-azoniabicyclo[2.2.2]octane chloride;

(3R)-1-[3-(Benzo[1,3]dioxol-5-yloxy)propyl]-3-(2-fur-2-yl-2-hydroxypent-3-ynoylamino)-1-azonia-bicyclo[2.2.2]octane bromide;

(3R)-1-[3-(Benzothiazol-2-yloxy)propyl]-3-(2-fur-2-yl-2-hydroxypent-3-ynoylamino)-1-azonia-bicyclo[2.2.2]octane chloride;

(3R)-3-{[(2S)-2-Cyclopentyl-2-hydroxy-2-thien-2-ylacetyl]amino}-1-(2-hydroxyethyl)-1-azoniabicyclo[2.2.2]octane bromide;

(3R)-3-{[(2S)-2-Cyclopentyl-2-hydroxy-2-thien-2-ylacetyl]amino}-1-(2-ethoxyethyl)-1-azoniabicyclo[2.2.2]octane formate;

(3R)-3-{[(2S)-2-Cyclopentyl-2-hydroxy-2-thien-2-ylacetyl]amino}-1-(4,4,4-trifluorobutyl)-1-azoniabicyclo[2.2.2]octane bromide;

(3R)-1-(4-Acetoxybutyl)-3-[2-(5-bromothien-2-yl)-2-(4-fluoro-3-methylphenyl)-2-hydroxyacetylamino]-1-azoniabicyclo[2.2.2]octane bromide;

(3R)-3-[2-(5-Bromothien-2-yl)-2-(4-fluoro-3-methylphenyl)-2-hydroxyacetylamino]-1-(4-ethoxycarbonylbutyl)-1-azoniabicyclo[2.2.2]octane bromide;

(3R)-1-(3-Acetylsulfanylpropyl)-3-[2-(5-bromothien-2-yl)-2-(4-fluoro-3-methylphenyl)-2-hydroxyacetylamino]-1-azoniabicyclo[2.2.2]octane formate;

(3R)-1-(3-Cyanopropyl)-3-[2-fur-2-yl-2-hydroxy-4-(4-methoxyphenyl)butyrylamino]-1-azoniabicyclo[2.2.2]octane bromide;

(3R)-1-(2-Carbamoylethyl)-3-[2-fur-2-yl-2-hydroxy-4-(4-methoxyphenyl)butyrylamino]-1-azoniabicyclo[2.2.2]octane formate; and (3R)-1-(2-[1,3]Dioxolan-2-yl-ethyl)-3-[2-fur-2-yl-2-hydroxy-4-(4-methoxyphenyl)butyrylamino]-1-azoniabicyclo[2.2.2]octane bromide.

8. A pharmaceutical composition comprising at least one compound according to claim 1 in admixture with at least one pharmaceutically acceptable carrier or diluent.

9. A combination product comprising,
(i) at least one first compound of claim 1; and
(ii) at least one second compound effective in the treatment of at least one pathological condition chosen from respiratory, urological, and gastrointestinal disease or disorder.

10. A combination product comprising,
(i) at least one first compound of claim 1; and
(ii) at least one second compound chosen from a $\beta_2$ agonist, a steroid, an antiallergic drug, a phosphodiesterase IV inhibitor, and a leukotriene D4 (LTD4) antagonist.

* * * * *

UNITED STATES PATENT AND TRADEMARK OFFICE
CERTIFICATE OF CORRECTION

PATENT NO. : 7,488,735 B2  Page 1 of 1
APPLICATION NO. : 10/518714
DATED : February 10, 2009
INVENTOR(S) : Maria Prat Quinones It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 791 days.

Signed and Sealed this

Seventh Day of September, 2010

David J. Kappos
*Director of the United States Patent and Trademark Office*